US009051369B2

(12) United States Patent
Lowenthal et al.

(10) Patent No.: US 9,051,369 B2
(45) Date of Patent: Jun. 9, 2015

(54) AVIAN CYTOKINES AND GENETIC SEQUENCES ENCODING SAME

(75) Inventors: John William Lowenthal, Belmont (AU); Andrew Gerard D. Bean, Ocean Grove (AU); Adam Joseph Karpala, Geelong (AU)

(73) Assignees: Commonwealth Scientific and Industrial Research Organisation, Campbell (AU); Australian Poultry CRC, Armidale (AU)

( * ) Notice: Subject to any disclaimer, the term of this patent is extended or adjusted under 35 U.S.C. 154(b) by 584 days.

(21) Appl. No.: 12/679,003

(22) PCT Filed: Sep. 19, 2008

(86) PCT No.: PCT/AU2008/001390
§ 371 (c)(1),
(2), (4) Date: Jun. 28, 2010

(87) PCT Pub. No.: WO2009/036510
PCT Pub. Date: Mar. 26, 2009

(65) Prior Publication Data
US 2011/0038834 A1 Feb. 17, 2011

Related U.S. Application Data

(60) Provisional application No. 60/994,567, filed on Sep. 20, 2007.

(51) Int. Cl.
*A61K 38/21* (2006.01)
*A61K 45/00* (2006.01)
*A01N 37/18* (2006.01)
*C07K 16/24* (2006.01)
*A61K 38/00* (2006.01)
*C07K 14/555* (2006.01)
*A61K 39/00* (2006.01)

(52) U.S. Cl.
CPC .............. *C07K 16/249* (2013.01); *A61K 38/00* (2013.01); *A61K 2039/505* (2013.01); *C07K 14/555* (2013.01); *C07K 2316/96* (2013.01); *C07K 2319/00* (2013.01)

(58) Field of Classification Search
None
See application file for complete search history.

(56) References Cited

U.S. PATENT DOCUMENTS 6,020,465 A * 2/2000 Sekellick et al. ............. 530/351
7,351,689 B2 * 4/2008 Doyle et al. ................. 424/85.2

FOREIGN PATENT DOCUMENTS

WO       02/086087 A2    10/2002
WO     2005/023862 A2    3/2005
WO     2007/041713 A1    4/2007

OTHER PUBLICATIONS

Wells, (1990), Biochemistry 29: pp. 8509-8517.*
Ngo et al., (1994), The Protein Folding Problem and Tertiary Structure Prediction, pp. 492-495.*
Abend et al., "Inhibitory Effect of Gamma Interferon on BK Virus Gene Expression and Replication, " *J. Virol.* 81(1):272-279, 2007.
Ank et al., "Lambda Interferon (IFN-λ), a Type III IFN, Is induced by Viruses and IFNs and Displays Potent Antiviral Activity against Select Virus Infections in Vivo," *J. Virol.* 80(9):4501-4509, 2006.
Annibali et al., "Gene expression profiles reveal homeostatic dynamics during interferon-β therapy in multiple sclerosis," *Autoimmunity* 40:16-22, 2007.
Beilharz et al., "Protection from lethal influenza virus challenge by oral type 1 interferon," *Biochemical and Biophysical Research Communications* 355740-744, 2007.
Bell et al., "Coral growing on North Sea oil rigs," *Nature* 402:601-602, 1999.
Bracci et al., "Type I IFN is a powerful mucosal adjuvant for a selective intranasal vaccination against influenza virus in mice and affects antigen capture at mucosal level," *Vaccine* 23:2994-3004, 2004.
Chen et al., "A survey of human cases of H5N1 avain influenza reported by the WHO before Jun. 2006 for infection control," *AJIC* 35(5): 351-353, 2007.
Chesler et al., "PKR Is Not Required for Interferon-γ Inhibition of VSV Replication in Neurons," *Viral Immunology* 16(1):87-96, 2003.
de Veer et al., "Functional classification of interferon-stimulated genes indentified using microarrays," *J. Leukoc. Biol.* 69:912-920, 2001.
Donnelly et al., "The expanded family of class II cytokines that share the IL-10 receptor-2 (IL-10R2) chain," *J. Leukoc. Biol.* 76:314-321, 2004.
Dumoutier et al., "Role of the Interleukin (IL)-28 Receptor Tyrosine Residues for Antiviral and Antiproliferative Activity of IL-29/Interferon-λ1," *J. Biol. Chem.* 279(31):32269-32274, 2004.

(Continued)

*Primary Examiner* — Christine J Saoud
*Assistant Examiner* — Jegatheesan Seharaseyon
(74) *Attorney, Agent, or Firm* — Seed IP Law Group PLLC

(57) ABSTRACT

The present invention relates generally to novel recombinant polypeptides having avian cytokine properties and to genetic sequences encoding same. More particularly, the present invention is directed to recombinant avian Type III interferon polypeptides, and genetic sequences encoding same, together with cellular expression systems and uses for same. Even more particularly, the present invention is directed to avian interferon-λ (IFN-λ) and functional derivatives, homologues and f

(56) References Cited

OTHER PUBLICATIONS

Green et al., "Analysis of Nitrate, Nitrite, and [$^{15}$N]Nitrate in Biological Fluids," *Analytical Biochemistry* 126:131-138, 1982.
Jacobs et al., "When Two Strands Are Better Than One: The Mediators and Modulators of the Cellular Responses to Double-Stranded RNA," *Virology* 219(0259):339-349, 1996.
Kaiser et al., "A Genomic Analysis of Chicken Cytokines and Chemokines," *J. Interferon & Cytokine Research* 25:467-484, 2005.
Karpala et al., "Molecular Cloning, Expression, and Characterization of Chicken IFN-λ," *J. Interferon & Cytokine Research* 28:341-350, 2008.
Koerner et al., "Protective Role of Beta Interferon in Host Defense against Influenza A Virus," *J. Virol.* 81(4):2025-2030, 2007.
Kotenko et al., "IFN-λs mediate antiviral protection through a distinct class II cytokine receptor complex," *Nature Immunology* 4(1):69-77, 2003.
Li et al., "Construction of Influenza Virus siRNA Expression Vectors and Their Inhibitory Effects on Multiplication of Influenza Virus," *Avian Diseases* 49:562-573, 2005.
Majde, "Viral Double-Stranded RNA, Cytokines, and the Flu," *J. Interferon and Cytokine Research* 20:259-270, 2000.
Marcello et al., "Interferons α and λ Inhibit Hepatitis C Virus Replication With Distinct Signal Transduction and Gene Regulation Kinetics," *Gastroenterology* 131:1887-1898, 2006.
Meager et al., "Biological activity of interleukins-28 and -29: Comparison with type I interferons," *Cytokine* 31:109-118, 2005.
Meager, "Biological assays for interferons," *J. Immunological Methods* 261:21-36, 2002.
Moraes et al., "Enhanced Antiviral Activity against Foot-and-Mouth Disease Virus by a Combination of Type I and II Porcine Interferons," *J. Virol* 81(13):7124-7135, 2007.
Robeck et al., "Lambda Interferon Inhibits Hepatitis B and C Virus Replication," *J. Virol* 79(6):3851-3854, 2005.
Schroder et al., "Interferon-γ: an overview of signals, mechanisms, and functions," *J. Leukoc. Biol.* 75:163-189, 2004.
Schultz et al., "The interferon system of non-mammalian vertebrates," *Development and Comparative Immunology* 28:499-508, 2004.
Sheppard et al., "IL-28, IL-29 and their class II cytokine receptor IL-28R," *Nature Immunology* 4(1):63-68, 2003.
Smith et al., "Type 1 interferons and the innate immune response-more than just antiviral cytokines," *Molecular Immunology* 42:869-877, 2005.
Sung et al., "L-Arginine-Dependent Production of a Reactive Nitrogen Intermediate by Macrophages of a Uricotelic Species," *J. Leukoc. Biol.* 50:49-56, 1991.
Takaoka et al., "Interferon signalling network in innate defence," *Cellular Microbiology* 8(6):907-922, 2006.
Tanabe et al., "Mechanism of up-regulation of human Toll-like receptor 3 secondary to infection of measles virus-attenuated strains," *Biochemical and Biophysical Research Communications* 311:39-48, 2003.
Theofilopoulos et al., "Type I Interferons (α/β) in Immunity and Autoimmunity," *Annu. Rev. Immunol.* 23:307-336, 2005.
Tissari et al., "IFN-α Enhances TRL3-Mediated Antiviral Cytokine Expression in Human Endothelial and Epithelial Cells by Up-Regulating TLR3 Expression," *J. Immunology* 174:4289-4294, 2005.
Zöller et al., "Sequence Comparison of Avian Interferon Regulatory Factors and Identification of the Avian CEC-32 Cell as a Quail Cell Line," *J. Interferon and Cytokine Research* 20:711-717, 2000.
Bowie et al., "Deciphering the Message in Protein Sequences: Tolerance to Amino Acid Substitutions," 247(4948):1306-1310, 1990.
GenBank Accession No. ABU82742.1, "interferon lambda [*Gallus gallus*]," Jun. 10, 2009, 1 page.
GenBank Accession No. ACC68984.1, "interleukin 28 [*Gallus gallus*]," Apr. 27, 2008, 1 page.
GenBank Accession No. AM773754.1, "*Gallus gallus* mRNA for interferon-lambda (IFNL gene), isolated from White Leghorn chicken," Jul. 18, 2008, 1 page.
Qian et al., "High-resolution structure prediction and the crystallographic phase problem," *Nature* 450:259-264, 2007.
Wan et al., "Epitope Map for a Growth Hormone Receptor Agonist Monoclonal Antibody, MAb 263," *Molecular Endocrinology* 17(11):2240-2250, 2003.

\* cited by examiner

FIGURE 2

```
SEQ ID NO:17  H.sapiens IFNλ2  IL28A
SEQ ID NO:18  M.musculus IL28A
SEQ ID NO:19  G.gallus IFNλ
SEQ ID NO:20  D.rerio IFNλ

H.sapiens IFNλ2  IL28A    MKLDMTGDCTPVLVLMAAVLTVTGA VPVARLHGALPDARGCHIAQFKSLS
M.musculus IL28A          -------MLLLLLPLLLAAVLTRTQA DPVPRATRLPVEAKDCHIAQFKSLS
G.gallus IFNλ             -------MVCYGVTIILVGTLGSLLVGA FPQVT----PKKSCSLSKYQFPA
D.rerio IFNλ              -------MTSKQKVFGSRGTRGRVWKRQPEIRWNQSQSSASTCEWLGRYR
                                                        .      .

H.sapiens IFNλ2  IL28A    PQELQAFKRAKDALEESLLLKDCRCHSRLFPRTWDLRQLQVRERPMALEA
M.musculus IL28A          PKELQAFKKAKGAIEKRLLEKDMRCSSHLISRAWDLKQLQVQERPKALQA
G.gallus IFNλ             PLELKAVWRMKEQFEDIMLLTNRKCNTRLFHRKWDIAELSVPDRITLVEA
D.rerio IFNλ              IITTESLNLLKNMGGKYADLETFFPSRLYFLMDKSKVEDQVKFLVLTLDH
                              *           .     .         .                ::

H.sapiens IFNλ2  IL28A    ELALTLKVLEATADTDPALVDVLDQPLHTLHHILSQFRACIQ-PQPTAGP
M.musculus IL28A          EVALTLKVWENINDS--ALTTILGQPLHTLSHIHSQLQTCTQ-LQATAEP
G.gallus IFNλ             ELDLTITVLTNPTTQR-LAETCQQPLAFITQVQEDLRDCLA-LEAPSHQ
D.rerio IFNλ              IIHLMDAREHMNSVN--WDQNTVEDFLNILHRKSSDLKECVARYAKPAHK
                           :   *           . *    * :   . ::::  .         ::

H.sapiens IFNλ2  IL28A    RTRG-RLHHWLYRLQEAPKKESPGCLEASVTFNLFRLLTRDLNCVASGDL
M.musculus IL28A          KPPSRRLSRWLHRLQEAQSKETPGCLEDSVTSNLFQLLLRDLKCVASGDQ
G.gallus IFNλ             --PSGKLRHWLQKLKTAKKKETAGCLEASAILHIFQVLN-DLRCAAQRED
D.rerio IFNλ              ESYEIRIKRHFRTLKKILKKQYSAEAWEQIRRVVKSHLQRMDIIASNAR
                            .    :   *:  :     ::     *   :

H.sapiens IFNλ2  IL28A    CV---
M.musculus IL28A          CV---
G.gallus IFNλ             CT---
D.rerio IFNλ              VNPRV
```

FIGURE 3

```
SEQ ID NO:1
SEQ ID NO:2

1   atggtatgct acgggtcac aattattttg gtggggaccc tgggtcccct cctgttgggt
      M  V  C  Y  G  V  T  I  I  L  V  G  T  L  G  S  L  L  V  G 61   gccttcccc  aggtcacccc gaagaagagc tgcagcctct ccaagtacca gttcctgca
      A  F  P  Q  V  T  P  K  K  S  C  S  L  S  K  Y  Q  F  P  A 121   cctttggagt tgaaggcagt gtggaggatg aaggagcagt ttgaagacat catgctgtta
      P  L  E  L  K  A  V  W  R  M  K  E  Q  F  E  D  I  M  L  L 181   acaaacagaa aatgcaacac cagactcttc catcggaagt gggacatagc tgagctgtcg
      T  N  R  K  C  N  T  R  L  F  H  R  K  W  D  I  A  E  L  S 241   gtacctgacc gaatcaccct ggtggaggct gagctggacg tcaccatcac cgtgctcaca
      V  P  D  R  I  T  Q  L  V  E  A  E  L  D  L  T  I  T  V  L  T 301   aaccccacaa cccagagact ggcagagacg tgccaacagc ccctggcctt ccttacccaa
      N  P  T  T  Q  R  L  A  E  T  C  Q  Q  P  L  A  F  L  T  Q 361   gtccaggagg acctgcgaga ctgcttggcc ctcgaggcac cttcacatca gccctctggg
      V  Q  E  D  L  R  D  C  L  A  L  E  A  P  S  H  Q  P  S  G 421   aaactgaggc actggctgca gaagctgaag acagccaaga agaaggagac cgccggctgc
      K  L  R  H  W  L  Q  K  L  K  T  A  K  K  K  E  T  A  G  C 481   ctggaggcct cagccatcct ccacatcttc caagtactga acgacctgcg gtgccgcagcc
      L  E  A  S  A  I  L  H  I  F  Q  V  L  N  D  L  R  C  A  A 541   cagcgcgagg attgcactta g
      Q  R  E  D  C  T  -
```

US 9,051,369 B2

AVIAN CYTOKINES AND GENETIC SEQUENCES ENCODING SAME

CROSS REFERENCE TO RELATED APPLICATIONS

This application claims the benefit and priority to and is a U.S. National Phase Application of PCT International Application Number PCT/AU2008/001390, filed on Sep. 19, 2008, designating the United States of America and published in the English language, which is an International Application of and claims the benefit of priority to U.S. Provisional Application No. 60/994,567, filed on Sep. 20, 2007. The disclosures of the above-referenced applications are hereby expressly incorporated by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 210190_401USPC_SEQUENCE_LISTING.txt. The text file is about 13.8 KB, was created on Jun. 19, 2013, and is being submitted electronically via EFS-Web.

FIELD OF THE INVENTION

The present invention relates generally to novel recombinant polypeptides having avian cytokine properties and to genetic sequences encoding same. More particularly, the present invention is directed to recombinant avian Type III interferon polypeptides, and genetic sequences encoding same, together with cellular expression systems and uses for same. Even more particularly, the present invention is directed to avian interferon-λ (IFN-λ) and functional derivatives, homologues and fragments thereof and to methods of use thereof. The molecules and cells of the present invention are useful in a wide range of applications including, but not limited to, providing a means for the treatment and prophylaxis of disease conditions, in particular avian disease conditions, or for use as an immune response modulator. Also provided are diagnostic means for screening for immune response and screening means for identifying modulators of IFN-λ protein or nucleic acid functionality.

BACKGROUND OF THE INVENTION

Bibliographic details of the publications referred to by author in this specification are collected alphabetically at the end of the description.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The rapidly increasing sophistication of recombinant DNA technology is greatly facilitating research into the medical and veterinary fields. Cytokine research is of particular importance, especially as these molecules regulate the proliferation, differentiation and function of a great variety of cells, such as cells involved in mediating an immune response. Administration of recombinant cytokines or regulating cytokine function and/or synthesis is becoming, increasingly, the focus of medical research into the treatment of a range of disease conditions in humans and animals.

Interferons (IFNs) represent a group of cytokines which cause diverse cellular effects in vertebrates by regulating hundreds of genes known as the IFN stimulated genes (ISG). IFNs exhibit multifunctional roles including the modulation of cellular growth cycles and the induction and regulation of inflammatory responses which largely shape the overall immune response. One of the most recognised attributes of IFNs is their ability to induce cellular resistance to virus (Hwang et al 1995, PNAS).

Vertebrate IFN consists of three types which are classified based on their molecular structure, receptor specificity and the pathways they induce (Smith et al., 2005; Theofilopoulos et al., 2005).

Type I IFN includes IFNα, of which there are multiple representatives in the vertebrate genomes (Meager, 2002), and IFNβ, usually represented by a single gene (Schultz et al., 2004). Type I IFNs are activated upon detection of many viruses (Jacobs and Langland 1996; Majde 2000) and once activated, interact with their receptor, the IFNα/β receptor (IFNα/βR), to induce a subset of the ISG which result in IFN-specific antiviral protection (de Veer et al., 2001; Takaoka and Yanai 2006). The therapeutic application of Type I IFN has been successful in protecting mammals from viruses, including influenza (Beilharz et al., 2007; Koerner et al., 2007), hepatitis C (Marcello et al., 2006) and several other viruses (Kotenko et al., 2003; Sheppard et al., 2003; Meager et al., 2005).

The Type II IFN group consists of a single member, IFNγ (Schroder et al., 2004). IFNγ activates antiviral activity and cellular immunity through the IFNγ receptor (IFN-γR) (Kamijo et al., 1994; Schroder, et al., 2004). This IFN also demonstrates antiviral activity, including protection from Foot and Mouth Disease (FMD) viruses (Moraes et al., 2007), polyomavirus (Abend et al., 2007), and others (Chesler et al., 2003) and has similarly been employed as a therapeutic against a variety of pathogens (Schroder et al., 2004).

Recently a third IFN family has been reported in mammals, Type III IFN, of which there are currently three known subtypes, these being IFNλ1 (also known as IL29), IFNλ2 (also known as IL28A) and IFNλ3 (also known as IL28B) (Sheppard, et al., 2003). The mammalian IFNλ members interact with a distinct receptor complex consisting of the IFNλ receptor 1 (IFNλR1) and the IL10 receptor β (IL10Rβ) (Donnelly et al., 2004). These subunit receptors dimerise upon ligand binding, phosphorylating the signal transducer and activator of transcription factors (STAT) (Kotenko et al., 2003; Donnelly et al., 2004) which results in the activation of an IFNλ-specific gene set (Ank et al., 2006; Marcello et al., 2006). Despite its IL10-like signalling complex (Sheppard et al., 2003; Donnelly et al., 2004) mammalian IFNλ exhibits antiviral properties that resemble Type I IFN (Meager et al., 2005). Hence, it appears that IFNλ may induce a subset of Type I IFN-like genes through an alternative receptor complex (Marcello et al., 2006).

Several investigations of human INFλ (HuIFNλ) have revealed the potential of IFNλ to inhibit virus. For example, HuIFNλII has been demonstrated to inhibit hepatitis C virus in mammalian cell culture (Robek et al., 2005; Marcello et al., 2006). This protection was comparable to Type I IFN, yet distinct gene subsets are initiated by each IFN (Marcello et al., 2006). Thus viral protection could be initiated from a different array of stimulated genes (Rio et al., 1998; Stohr and Esveld, 2004; Meager et al., 2005; Annibali et al., 2007). In addition, comparisons of the antiviral properties of IFNλ and Type I IFN demonstrates that both types of IFN are able to inhibit EMCV. However, the effects largely differed in magnitude (Meager et al., 2005). Similar findings were observed in research involving VSV (Kotenko et al., 2003). This suggests that the INFλ response pathway may be necessary for a specific functional role in certain viral infections.

There has recently been a great deal of concern with regard to poultry viruses with the observed outbreaks of avian influenza which can spread rapidly and cause high morbidity in both poultry and human populations (Stohr and Esveld 2004). The difficult task of managing problem viruses in poultry combined with the fact that associated immunotoxicity effects may be observed with the use of Type I and Type II IFN therapeutics (Kotenko et al., 2003; Stohr and Esveld 2004; Meager et al., 2005) necessitates an ongoing investigation for new and alternative antiviral strategies. Accordingly, there is a need for an improved control of poultry viruses which would benefit the poultry industries as well as help to reduce the risk of transmission of these viruses to humans (Chen et al., 2007). Still further, in light of the importance of the poultry industry to the economics and food supplies of communities world-wide, the development of new means for regulating and improving immunomodulation is of critical importance.

In the work leading up to the present invention, the nucleic acid molecule which encodes chicken IFN-λ (hereinafter referred to as "ChIFN-λ") has been isolated and sequenced. Recombinant genetic constructs comprising the isolated nucleic acid molecule of the present invention have been produced and expressed in transformed cells, thereby enabling the isolation and sequencing of ChIFN-λ. These findings now provide an opportunity for alternative IFN therapies.

SUMMARY OF THE INVENTION

Throughout this specification and the claims that follow, unless the context requires otherwise, the word "comprise", or variations such as "comprises" or "comprising" will be understood to imply the inclusion of a stated element or integer or group of elements or integers, but not the exclusion of any other element or integer or group of elements or integers.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

The subject specification contains amino acid and nucleotide sequence information prepared using the programme PatentIn Version 3.1, presented herein after the bibliography. Each amino acid and nucleotide sequence is identified in the sequence listing by the numeric indicator <210> followed by the sequence identifier (eg. <210>1, <210>2, etc). The length, type of sequence (amino acid, DNA, etc.) and source organism for each sequence is indicated by information provided in the numeric indicator fields <211>m<212> and <213>, respectively. Amino acid and nucleotide sequences referred to in the specification are identified by the indicator SEQ ID NO: followed by the sequence identifier (eg. SEQ ID NO:1, SEQ ID NO: 2, etc). The sequence identifier referred to in the specification correlates to the information provided in numeric indicator field <400> in the sequence listing, which is followed by the sequence identifier (eg. <400>1, <400>2, etc). That is SEQ ID NO: 1 as detailed in the specification correlates to the sequence indicated as <400>1 in the sequence listing.

Single and three letter abbreviations used throughout the specification are defined in Table 1.

One aspect of the present invention is directed to a nucleic acid molecule which encodes, or is complementary to a nucleic acid molecule which encodes, an avian cytokine polypeptide or a functional fragment or derivative thereof, wherein said polypeptide is a Type III interferon.

Another aspect of the present invention provides a nucleic acid molecule or functional fragment or derivative thereof which encodes, or is complementary to a nucleic acid molecule which encodes, an avian cytokine polypeptide or a functional fragment or derivative thereof, wherein said polypeptide is a Type III interferon and wherein said avian species is poultry selected from the list comprising chickens, ducks, geese, turkeys, bantams, quails or guinea fowl.

In another aspect, said Type III interferon polypeptide is a chicken IFN-λ (ChIFNλ) polypeptide or a fusion molecule comprising same or a functional fragment, derivative or avian homologue thereof.

In yet another aspect, there is provided a nucleic acid molecule or functional fragment or derivative thereof which encodes, or is complementary to a nucleic acid molecule which encodes, a chicken IFN-λ polypeptide or a functional fragment or derivative thereof.

Yet another aspect of the present invention is directed to an isolated nucleic acid selected from the list consisting of:
(i) An isolated nucleic acid molecule or functional fragment, derivative or avian homologue thereof comprising a nucleotide sequence encoding, or complementary to a sequence encoding, an amino acid sequence substantially as set forth in SEQ ID NO:2 or 4 or a functional derivative, fragment or avian homologue thereof, or an amino acid sequence having at least 50%, 60%, 65%, 70%, 75%, 80%, 85%, 90%, 95%, 96%, 97%, 98%, 99% or more sequence identity to SEQ ID NO:2 or 4 over the length of the sequence or a nucleic acid sequence capable of hybridizing to said nucleic acid molecule under low stringency conditions.
(ii) An isolated nucleic acid molecule or functional fragment derivative or avian homologue thereof comprising a nucleotide sequence, or complementary to said sequence, wherein said nucleotide sequence is substantially as set forth in SEQ ID NO:1 or 3 or a nucleotide sequence having at least about 50%, 55%, 60%, 65%, 70%, 75%, 80%, 85%, 90%, 95%, 96%, 97%, 98%, 99% or more identity over the length of the sequence or a nucleotide sequence capable of hybridising to SEQ ID NO:1 or 3 or complementary form thereof under low stringency conditions.
(iii) An isolated nucleic acid molecule or functional derivative, fragment or avian homologue thereof comprising a nucleotide sequence as set forth in SEQ ID NO:1 or 3.

Still another aspect of the present invention provides an avian interferon Type III polypeptide, or a functional fragment or derivative thereof.

Yet another aspect of the present invention is directed to an isolated protein as set forth in SEQ ID NO:2 or 4 or having at least about 60%, 65%, 75%, 80% or greater identity to SEQ ID NO:2 or 4 across the length of the sequence or a functional derivative, fragment or avian homologue thereof.

Still another aspect of the present invention is directed to a protein encoded by a nucleotide sequence as set forth in SEQ ID NOs:1 or 3 or the sequence complementary to a sequence capable of hybridising to SEQ ID NOs:1 or 3 under low stringency conditions and which encodes an amino acid sequence as set forth in SEQ ID NOs:2 or 4 or having at least about 60%, 65%, 70%, 75%, 80% or greater identity to SEQ ID NOs:2 or 4 across the length of the sequence.

A further aspect of the invention provides a method of producing a recombinant avian Type III interferon molecule in a cell, said method comprising expressing in said cell a nucleic acid molecule which encodes or is complementary to a nucleic acid molecule which encodes said avian Type III interferon.

A further aspect of the invention provides an isolated cell which expresses an endogenous or recombinant avian Type III interferon or a functional fragment, derivative or homologue thereof.

In a related aspect, the present invention provides a method of producing a recombinant avian Type III interferon in a cell comprising the steps of:
(i) introducing into said cell a genetic construct comprising a nucleic acid molecule which encodes or is complementary to a nucleic acid molecule which encodes said avian Type III interferon, placed under the control of a suitable promoter sequence;
(ii) culturing said cell for a time and under conditions sufficient for said nucleic acid molecule to be expressed; and
(iii) isolating said expression product.

In a further aspect, the present invention extends to a method of producing an avian Type III interferon fusion molecule in a cell, said method comprising introducing into said cell a genetic construct comprising a nucleic acid molecule which encodes or is complementary to a nucleic acid molecule which encodes an avian Type III interferon polypeptide or a functional fragment, derivative or avian homologue thereof, wherein said polypeptide is a fusion polypeptide between a first Type III interferon and a second Type III interferon or a first Type III interferon and a second Type I or Type II interferon selected from the list comprising IFN-α, IFN-β, IFN-γ, Ch IFN-α, Ch IFN-β, or Ch IFN-γ amongst others.

In yet another related aspect the present invention extends to a recombinant fusion polypeptide between a first Type III interferon and a second Type III interferon or a first Type III interferon and a second Type I or Type II interferon selected from the list comprising IFN-α, IFN-β, IFN-γ, ChIFN-α, ChIFN-β or ChIFN-γ amongst others.

Yet still another aspect of the present invention extends to a genetic construct comprising a nucleic acid molecule which encodes or is complementary to a nucleic acid molecule which encodes an avian Type III interferon fusion polypeptide or a functional fragment or derivative thereof, wherein said polypeptide is a fusion polypeptide between a Type III interferon and either a second Type III interferon or a first Type III interferon and a second Type I or Type II interferon selected from the list comprising IFN-α, IFN-β, IFN-γ, Ch IFN-α, Ch IFN-β, or Ch IFN-γ amongst others.

Yet another aspect of the present invention provides a method for identifying an avian Type III interferon genetic sequence, or a functional fragment or derivative thereof.

Still yet another aspect of the invention provides a method for detecting the presence of an avian Type III interferon polypeptide or a functional fragment, derivative or homologue thereof.

A further aspect of the present invention provides a method of treatment or prophylaxis of an aves said method comprising administering to said aves an effective amount of an avian Type III interferon polypeptide or a functional fragment, derivative or homologue thereof for a time and under conditions sufficient to maintain, stimulate or enhance the immunoresponsiveness of said aves.

In still another further aspect of the present invention there is provided a method of treatment or prophylaxis of an aves, which aves has been exposed to or infected with a pathogenic organism, said method comprising administering to said aves an effective amount of an avian Type III interferon polypeptide or a functional fragment, derivative, or homologue thereof.

Yet still another further aspect of the present invention relates to avian interferon III polypeptide for use in therapy or prophylaxis of an aves.

A still further aspect of the present invention relates to the use of an avian Type III interferon polypeptide in the manufacture of a medicament for the modulation of an immune response in an aves and/or for the treatment or prophylaxis of an aves.

Another aspect of the present invention provides an adjuvant comprising an avian cytokine molecule, wherein said cytokine is a Type III interferon or a fusion molecule between said Type III interferon molecule and a second cytokine molecule and optionally, a pharmaceutically-acceptable carrier, excipient or diluent.

Yet another aspect extends to a veterinary pharmaceutical composition comprising an immunomodulatory effective amount of an avian Type III interferon or a fusion molecule between an avian Type III interferon and a second cytokine or a genetic sequence capable of expressing same and one or more carriers and/or diluents acceptable for veterinary use.

TABLE 1

Single and three letter amino acid abbreviations

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | The | T |
| Tryptophan | Trp | W |
| Tyrosine | Tyr | Y |
| Valine | Val | V |
| Any residue | Xaa | X |

BRIEF DESCRIPTION OF THE DRAWINGS

FIG. 2 is a schematic representation of an alignment of the deduced amino acid sequence of ChIFNλ and IFNλII of various vertebrate species generated using ClustalW (BioManager). The predicted protein sequence of ChIFNλ was aligned with HuIFNλII (accession no. NM_172138), mIFN-λII (accession no. AY869695) and fishIFNλ (accession no. AB093588). The identical amino acid residues are marked '*', while conserved and semi-conserved residues are depicted by ':' and '.', respectively. Dashes indicate gaps introduced into the sequence to optimise the alignment. Signal peptides were identified and are shown in the boxes, however, no signal peptide could be predicted for fishIFNλ.

FIG. 3 is a schematic representation of the ChIFNλ nucleotide sequence and predicted amino acid translation. The ORF of ChIFNλ was sequence analysed and the predicted amino acid translation is shown. The predicted signal peptide is underlined and intron splice locations are identified by the arrows.

Figure 1:
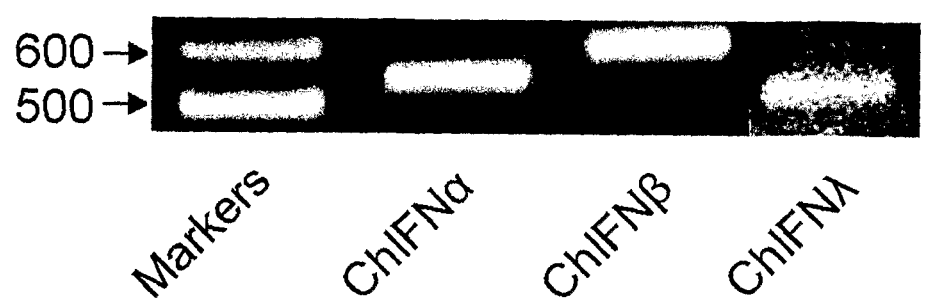
FIG. 1 is an image of RT-PCR expression analysis of ChIFN transcripts from chicken splenocytes treated with Poly (I:C) (50 µg/ml) for 2 h. ChIFNα, β or λ were amplified using IFN-specific sequencing primers and run on a 1% agarose gel. Water was included as a negative control. Expression of GAPDH was included as an internal control.

Accordingly, one aspect of the present invention is directed to a nucleic acid molecule which encodes, or is complementary to a nucleic acid molecule which encodes, an avian cytokine polypeptide or a functional fragment or derivative thereof, wherein said polypeptide is a Type III interferon.

The term "avian" should be understood to encompass a member of the class of vertebrates commonly referred to as birds. It should be understood that as used herein, the term "avian" includes both sexes and all developmental stages of poultry species, domestic birds and game birds selected from the list comprising chickens, turkeys, bantams, quails, guinea fowl, ducks, geese, ostriches, emus, pigeons, canaries, budgerigars, parrots and finches, amongst others.

Herein reference to the term "cytokine polypeptide" should be understood to refer to a polypeptide molecule comprising at least one subunit of a biologically-active protein which possesses one or more of the characteristic biological features of a Type III interferon, in particular the ability to modulate the functionality of an avian immune cell, such as a lymphocyte (B or T cell), granulocyte (eosinephil, basophil or neutrophil) or other non-specific immune cell (e.g. macrophage, monocyte, NK cell or the like).

Without limiting the present invention to any one theory or mode of action, it has been determined that Type III interferons exhibit biological properties that resemble those of Type I interferon. Accordingly, reference to the biological activity of a Type III interferon should be understood as including but not limited to, antiviral and immunostimulatory activities such as for example, virus induced expression which leads to signalling via the Janus kinase (Jak)-STAT signal-transduction pathway and activation of IFN-stimulated regulated gene expression (ISRE), upregulation of major histocompatibility complex (MHC) class I antigen expression and protection against the cytopathic effects induced by virus infection.

Accordingly, another aspect of the present invention provides a nucleic acid molecule or functional fragment or derivative thereof which encodes, or is complementary to a nucleic acid molecule which encodes, an avian cytokine polypeptide or a functional fragment or derivative thereof, wherein said polypeptide is a Type III interferon and wherein said avian species is a chicken, turkey, bantam, quail, guinea fowl, duck, goose, ostrich, emu, pigeon, canary, budgerigar, parrot or finch.

Most preferably, the nucleic acid molecule of the present invention is derived from chickens.

Without limiting the present invention to any one theory or mode of action, and as detailed hereinbefore, IFNs are classified into three families based on molecular structure, receptor type and the functional pathways that they induce. These families are IFN-I, IFN-II and IFN-III. Type III IFNs encompass the IFN lambda (λ) group of which, in the mammal, there are three subtypes, IFNλ1 (IL29), IFNλ2 (IL28A), and IFNλ3 (IL28B). While the INF-λ group in the chicken appears to only comprise one member, it should be understood that reference to avian IFN-λ encompasses reference to all forms of these molecules and to functional fragments, derivatives, and avian homologues thereof, including isomeric forms which may arise from alternative splicing of IFN-λ mRNA, polymorphic forms, allelic forms and to forms existing as dimers, multimers and fusion proteins. Without limiting the present invention to any one theory or mode of action, the IFN-λ gene preferably comprises 5 exonic regions on chromosome 7 which encodes a 186 amino acid polypeptide with a molecular weight of 21 kDa, that exhibits only 36% identity to HuIFNλII at the nucleotide level. The expression product of the IFN-λ gene preferably exhibits antiviral and immunostimulatory activity as hereinbefore described.

In a preferred embodiment, said Type III interferon polypeptide is a chicken IFN-λ (ChIFNλ) polypeptide or a fusion molecule comprising same or a functional fragment, derivative or avian homologue thereof.

According to this preferred embodiment, there is provided a nucleic acid molecule or functional fragment or derivative thereof which encodes, or is complementary to a nucleic acid molecule which encodes, a chicken IFN-λ polypeptide or a functional fragment, avian homologue or derivative thereof.

Yet another aspect of the present invention is directed to an isolated nucleic acid selected from the list consisting of:

(i) An isolated nucleic acid molecule or functional fragment, derivative or avian homologue thereof comprising a nucleotide sequence encoding, or complementary to a sequence encoding, an amino acid sequence substantially as set forth in SEQ ID NO:2 or 4 or a functional derivative, fragment or avian homologue thereof, or an amino acid sequence having at least 50%, 60%, 65%, 70%, 75%, 80%, 85%, 90%, 91%, 92%, 93%, 94%, 95%, 96%, 97%, 98%, 99% or more sequence identity to SEQ ID NO:2 or 4 over the length of the sequence or a nucleic acid sequence capable of hybridizing to said nucleic acid molecule under low stringency conditions.

(ii) An isolated nucleic acid molecule thereof comprising a nucleotide sequence, or complementary to said sequence, wherein said nucleotide sequence is substantially as set forth in SEQ ID NO:1 or 3 or a nucleotide sequence having at least about 50%, 55%, 60%, 65%, 70%, 75%, 80%, 85%, 90%, 91%, 92%, 93%, 94%, 95%, 96%, 97%, 98%, 99% or more identity over the length of the sequence or a nucleotide sequence capable of hybridising to SEQ ID NO:1 or 3 or complementary form thereof under low stringency conditions.

(iii) An isolated nucleic acid molecule or functional derivative, fragment or avian homologue thereof comprising a nucleotide sequence as set forth in SEQ ID NO:1 or 3 or a functional fragment of said molecule.

The present invention should be understood to extend to the genomic DNA form of the cDNA nucleotide sequences detailed above. To this end, SEQ ID NO:1 corresponds to ChIFNλ cDNA, including the sequence encoding the signal peptide. SEQ ID NO:3 corresponds to the sequence encoding the ChIFNλ cDNA open reading frame of the mature protein, i.e. the protein without the signal sequence. SEQ ID NO:2 corresponds to the ChIFNλ protein which includes the signal sequence while SEQ ID NO:4 corresponds to the ChIFNλ protein which does not include the signal sequence.

Reference herein to the genomic and cDNA forms of ChIFNλ is to be understood in its broadest context and includes:

(i) a classical genomic gene consisting of transcriptional and/or translational regulatory sequences and/or a coding region and/or non-translated sequences (i.e. introns, 5'- and 3'-untranslated sequences);

(ii) mRNA or cDNA corresponding to the coding regions (i.e. exons) optionally comprising 5'- or 3'-untranslated sequences of the gene; and/or (iii) mRNA or cDNA corresponding to the coding region either with or without sequences associated with precursor forms of the protein, such as signal sequences, and optionally 5'- or 3'-untranslated sequences.

As hereinbefore described, ChIFNλ corresponds to a previously unidentified avian interferon molecule. It should be understood that the present invention also extends to the expression product of the nucleic acid molecule as hereinbefore defined.

Accordingly, another aspect of the present invention is directed to an avian cytokine polypeptide or a functional fragment or derivative thereof, wherein said polypeptide is a Type III interferon.

Preferably, said avian interferon Type III polypeptide is an avian IFN-λ polypeptide or a functional fragment or derivative thereof.

More preferably said IFN-λ polypeptide is ChIFN-λ

Yet another aspect of the present invention is directed to an isolated protein as set forth in SEQ ID NO:2 or 4 or having at least about 60%, 65%, 75%, 80% or greater identity to SEQ ED NO:2 or 4 across the length of the sequence or a functional derivative, fragment or avian homologue thereof.

The term "protein" should be understood to encompass peptides, polypeptides and proteins. It should also be understood that these terms are used interchangeably herein. The protein may be glycosylated or unglycosylated and/or may contain a range of other molecules fused, linked, bound or otherwise associated to the protein such as amino acids, lipids, carbohydrates or other peptides, polypeptides or proteins. Reference hereinafter to a "protein" includes a protein comprising a sequence of amino acids as well as a protein associated with other molecules such as amino acids, lipids, carbohydrates or other peptides, polypeptides or proteins.

Preferably, said 60% or greater similarity is a reference to 65%, 75%, 80%, 85%, 90%, 91%, 92%, 93%, 94%, 95%, 96%, 97%, 98% or 99% similarity.

The protein of the present invention is preferably in isolated form. By "isolated" is meant a protein having undergone at least one purification step and this is conveniently defined, for example, by a composition comprising at least about 10% subject protein, preferably at least about 20%, more preferably at least about 30%, still more preferably at least about 40-50%, even still more preferably at least about 60-70%, yet even still more preferably 80-90% or greater of subject protein relative to other components as determined by molecular weight, amino acid sequence or other convenient means. The protein of the present invention may also be considered, in a preferred embodiment, to be biologically pure.

As used herein, in terms of both the claimed proteins and nucleic acid molecules, the term "isolated" means that the material is removed from its original environment (e.g., the natural environment if it is naturally occurring). For example, a naturally occurring polynucleotide or protein present in a living animal is not isolated, but the same polynucleotide or protein, separated from some or all of the coexisting materials in the natural system, is isolated. Such polynucleotides could be part of a vector and/or such polynucleotides or protein could be part of a composition, and still be isolated in that such vector or composition is not part of its natural environment. As used herein, an isolated material or composition can also be a "purified" composition, i.e., it does not require absolute purity; rather, it is intended as a relative definition. Individual nucleic acids obtained from a library can be conventionally purified to electrophoretic homogeneity. In alternative aspects, the invention provides nucleic acids which have been purified from genomic DNA or from other sequences in a library or other environment by at least one, two, three, four, five or more orders of magnitude.

Proteins of the invention can be isolated from natural sources, be synthetic, or be recombinantly generated polypeptides. Peptides and proteins can be recombinantly expressed in vitro or in vivo. The proteins of the invention can be made and isolated using any method known in the art. Proteins of the invention can also be synthesized, whole or in part, using chemical methods well known in the art. See e.g., Caruthers et al. (1980) *Nucleic Acids Res. Symp. Ser.* 215-223; Horn et al. (1980) *Nucleic Acids Res. Symp. Ser.* 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge et al. (1995) *Science* 269:202; Merrifield (1997) *Methods Enzymol.* 289:3-13) and automated synthesis may be achieved, e.g., using the ABI 431A Peptide Synthesizer (Perkin Elmer) in accordance with the instructions provided by the manufacturer.

Proteins of the invention can also be synthesised and expressed as fusion proteins with one or more additional domains linked thereto for, e.g., to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising protein to facilitate purification. For example, an expression vector can include an epitope-encoding nucleic acid sequence linked to six histidine residues followed by a thioredoxin and an enterokinase cleavage site (see e.g., Williams et al. (1995) *Biochemistry* 34:1787-1797; Dobeli et al. (1998) *Protein Expr. Purif.* 12:404-14). The histidine residues facilitate detection and purification while the enterokinase cleavage site provides a means for purifying a region from the remainder of the fusion protein. Technology pertaining to vectors encoding fusion proteins and application of fusion proteins are well described in the scientific and patent literature, see e.g., Kroll et al. (1993) *DNA Cell. Biol.*, 12:441-53.

Notwithstanding that the present invention encompasses recombinant proteins, chemical synthetic techniques are also contemplated in the synthesis of the subject proteins.

A chemically synthesised polypeptide according to the present invention is conveniently synthesised based on molecules isolated from avian sources. Isolation of the avian molecules may be accomplished by any suitable means such as by chromatographic separation, for example using CM-cellulose ion exchange chromatography followed by Sephadex (e.g. G-50 column) filtration. Many other techniques are available including HPLC, PAGE amongst others.

Preferably the chemically synthesised polypeptide of the present invention is conveniently synthesised based on molecules isolated from the chicken.

The subject polypeptide may be synthesised by solid phase synthesis using F-moc chemistry as described by Carpino et al. (1991). polypeptides and fragments thereof may also be synthesised by alternative chemistries including, but not limited to, t-Boc chemistry as described in Stewart et al. (1985) or by classical methods of liquid phase peptide synthesis.

Still another aspect of the present invention is directed to a protein encoded by a nucleotide sequence as set forth in SEQ ID NOs:1 or 3 or the sequence complementary to a sequence capable of hybridising to SEQ ID NOs:1 or 3 under low stringency conditions and which encodes an amino acid sequence as set forth in SEQ ID NOs:2 or 4 or having at least about 60%, 65%, 70%, 75%, 80% or greater identity to SEQ ID NOs:2 or 4 across the length of the sequence.

The subject invention clearly contemplates a related or homologues Type III interferon gene or protein derived from an avian source other than just chickens, such as but not limited to, any poultry species, domestic bird or game bird selected from the list comprising turkeys, bantams, quails, guinea fowl, ducks, geese, ostriches, emus, pigeons, canaries, budgerigars, parrots and finches, amongst others. The present invention extends further to said avian Type III interferon genes derived from embryo tissues or cultured cells.

Reference herein to "Type III interferon" should be understood as a reference to the nucleic acid and protein molecules hereinbefore described.

The phrases "nucleic acid" or "nucleic acid sequence" as used herein refer to an oligonucleotide, nucleotide, polynucleotide, or to a fragment of any of these, to DNA or RNA (e.g., mRNA, rRNA, tRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., iRNPs). The term encompasses nucleic acids, i.e., oligonucleotides, containing known analogues of natural nucleotides. The term also encompasses nucleic-acid-like structures with synthetic backbones, see e.g., Mata (1997) *Toxicol. Appl. Pharmacol.* 144:189-197; Strauss-Soukup et al. (1997) *Biochemistry* 36:8692-8698; Samstag et al. (1996) *Antisense Nucleic Acid Drug Dev* 6:153-156.

To this end, it should be understood that the present invention extends to antisense nucleic acid molecules which are directed to the avian cytokine nucleic acid molecules herein defined.

An "expression product" includes an RNA molecule such as an mRNA transcript as well as a protein. Some genes are non-protein encoding genes and produce mRNA or other RNA molecules and are involved in regulation by RNA:DNA, RNA:RNA or RNA:protein interaction. The RNA (e.g. mRNA) may act directly or via the induction of other molecules such as RNAi or via products mediated from splicing events (e.g. exons or introns). Short, interfering RNA (siRNA) is also contemplated by the present invention. Other genes encode mRNA transcripts which are then translated into proteins. A protein includes a polypeptide. The differentially expressed nucleic acid molecules, therefore, may encode mRNAs only or, in addition, proteins. Both mRNAs and proteins are forms of "expression products".

A further aspect of the invention provides a method of producing a recombinant avian Type III interferon molecule in a cell, said method comprising expressing in said cell a nucleic acid molecule which encodes or is complementary to a nucleic acid molecule which encodes said avian Type III interferon.

The nucleic acid molecule of the present invention is preferably in isolated form or ligated to a vector, such as an expression vector. By "isolated" is meant a nucleic acid molecule having undergone at least one purification step and this is conveniently defined, for example, by a composition comprising at least about 10% subject nucleic acid molecule, preferably at least about 20%, more preferably at least about 30%, still more preferably at least about 40-50%, even still more preferably at least about 60-70%, yet even still more preferably 80-90% or greater of subject nucleic acid molecule relative to other components as determined by molecular weight, amino acid sequence or other convenient means. The nucleic acid molecule of the present invention may also be considered, in a preferred embodiment, to be biologically pure.

The nucleic acids of the invention can be made, isolated and/or manipulated by, e.g., cloning and expression of cDNA libraries, amplification of message or genomic DNA by PCR, and the like. In practicing the methods of the invention, homologous genes can be modified by manipulating a template nucleic acid, as described herein. The invention can be practiced in conjunction with any method or protocol or device known in the art, which are well described in the scientific and patent literature.

The nucleic acids used to practice this invention, whether RNA, iRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) *J. Am. Chem. Soc.* 105:661; Belousov et al. (1997) supra; Frenkel et al. (1995) supra; Blommers et al. (1994) supra; Narang et al. (1979) *Meth. Enzymol.* 68:90; Brown et al. (1979) *Meth. Enzymol.* 68:109; Beaucage (1981) *Tetra. Lett.* 22:1859; U.S. Pat. No. 4,458,066.

The invention provides oligonucleotides comprising sequences of the invention, e.g., subsequences of the exemplary sequences of the invention. Oligonucleotides can include, e.g., single stranded poly-deoxynucleotides or two complementary polydeoxynucleotide strands which may be chemically synthesized.

Techniques for the manipulation of nucleic acids, such as, e.g., subcloning, labelling probes (e.g., random-primer labelling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immuno-electrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), nucleic acid or target or signal amplification methods, radiolabelling, scintillation counting, and affinity chromatography.

Obtaining and manipulating nucleic acids used to practice the methods of the invention can be done by cloning from genomic samples, and, if desired, screening and re-cloning inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; yeast artificial chromosomes (YAC); bacterial artificial chromosomes (BAC); P1 artificial chromosomes, see, e.g., Woon et al. (1998) *Genomics* 50:306-316; P1-derived vectors (PACs), see, e.g., Kern (1997) *Biotechniques* 23:120-124; cosmids, recombinant viruses, phages or plasmids.

The nucleic acids of the invention can be operatively linked to a promoter. A promoter can be one motif or an array of nucleic acid control sequences which direct transcription of a nucleic acid. A promoter can include necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The invention provides expression vectors and cloning vehicles comprising nucleic acids of the invention, e.g., sequences encoding the proteins of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors of the invention can include chromosomal, non-chromosomal and synthetic DNA sequences. Large numbers of suitable vectors are known to those of skill in the art, and are commercially available.

The nucleic acids of the invention can be cloned, if desired, into any of a variety of vectors using routine molecular biological methods; methods for cloning in vitro amplified nucleic acids are described, e.g., U.S. Pat. No. 5,426,039. To facilitate cloning of amplified sequences, restriction enzyme sites can be "built into" a PCR primer pair.

The invention provides libraries of expression vectors encoding polypeptides and peptides of the invention. These nucleic acids may be introduced into a genome or into the cytoplasm or a nucleus of a cell and expressed by a variety of conventional techniques, well described in the scientific and patent literature. See, e.g., Roberts et al. (1987) *Nature* 328: 731; Schneider (1995) *Protein Expr. Purif.* 6435:10; Sambrook, Tijssen or Ausubel. The vectors can be isolated from natural sources, obtained from such sources as ATCC or GenBank libraries, or prepared by synthetic or recombinant methods. For example, the nucleic acids of the invention can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required.

In one aspect, the nucleic acids of the invention are administered in vivo for in situ expression of the peptides or polypeptides of the invention. The nucleic acids can be administered as "naked DNA" (see, e.g., U.S. Pat. No. 5,580,859) or in the form of an expression vector, e.g., a recombinant virus. The nucleic acids can be administered by any route, including peri- or intra-tumorally, as described below. Vectors administered in vivo can be derived from viral genomes, including recombinantly modified enveloped or non-enveloped DNA and RNA viruses, preferably selected from baculoviridiae, parvoviridiae, picornoviridiae, herpesveridiae, poxyiridae, adenoviridiae, or picornnaviridiae. Chimeric vectors may also be employed which exploit advantageous merits of each of the parent vector properties (See e.g., Feng et al. (1997) *Nature Biotechnology* 15:866-870). Such viral genomes may be modified by recombinant DNA techniques to include the nucleic acids of the invention; and may be further engineered to be replication deficient, conditionally replicating or replication competent. In alternative aspects, vectors are derived from the adenoviral (e.g., replication incompetent vectors derived from the human adenovirus genome, see, e.g., U.S. Pat. Nos. 6,096,718; 6,110,458; 6,113,913; 5,631,236); adeno-associated viral and retroviral genomes. Retroviral vectors can include those based upon murine leukemia virus (MuLV), gibbon ape leukemia virus (GaLV), Simian Immuno deficiency virus (SIV), human immuno deficiency virus (HIV), and combinations thereof; see, e.g., U.S. Pat. Nos. 6,117,681; 6,107,478; 5,658,775; 5,449,614; Buchscher and Panganiban (1992) *J. Virol.* 66:2731-2739; Johann et al. (1992) *J. Virol.* 66:1635-1640). Adeno-associated virus (AAV)-based vectors can be used to transduce cells with target nucleic acids, e.g., in the in vitro production of nucleic acids and peptides, and in in vivo and ex vivo gene therapy procedures; see, e.g., U.S. Pat. Nos. 6,110,456; 5,474,935; Okada et al. (1996) *Gene Ther.* 3:957-964.

The term "expression cassette" as used herein refers to a nucleotide sequence which is capable of affecting expression of a structural gene (i.e., a protein coding sequence, such as a polypeptide of the invention) in a host compatible with such sequences. Expression cassettes include at least a promoter operably linked with the polypeptide coding sequence; and, optionally, with other sequences, e.g., transcription termination signals. Additional factors necessary or helpful in effecting expression may also be used, e.g., enhancers. "Operably linked" as used herein refers to linkage of a promoter upstream from a DNA sequence such that the promoter mediates transcription of the DNA sequence. Thus, expression cassettes also include plasmids, expression vectors, recombinant viruses, any form of recombinant "naked DNA" vector, and the like.

A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and includes both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

For optimum expression in a particular tissue or under specified conditions, the nucleic acid molecule may be placed operably under the control of a promoter sequence such as those discussed supra. Suitable cells and virus particles for this purpose are also discussed supra. Promoter sequences and culture conditions for cells or virus particles which produce high levels of expression will be well-known to those skilled in the relevant art.

The invention also provides a transformed cell comprising a nucleic acid sequence of the invention, e.g., a sequence encoding a polypeptide of the invention, or a vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Salmonella typhimurium* and various species within the genera *Pseudomonas, Streptomyces,* and *Staphylococcus*. Exemplary insect cells include *Drosophila* S2 and *Spodoptera* SD. Exemplary animal cells include CHO, COS or Bowes melanoma or any mouse or human cell line. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation.

Engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Accordingly, a further aspect of the invention provides an isolated cell which expresses an endogenous or recombinant avian Type III interferon or a functional fragment, derivative or homologue thereof.

In a most preferred embodiment, the avian Type III interferon molecule according to this aspect of the invention is avian IFN-λ, in particular ChIFN-λ.

Alternatively, the isolated cell may be a transformed eukaryotic cell which expresses a Type III interferon molecule via a genetic construct, such as those discussed earlier. Means for introducing genetic constructs into a cell have been defined herein and will be well-known to those skilled in the art.

Means for isolating a cell which expresses an endogenous or recombinant avian Type III interferon have also been discussed herein and will be well-known to those skilled in the art.

The terms "similarity" and "identity" as used herein include exact identity between compared sequences at the nucleotide or amino acid level. Where there is non-identity at the nucleotide level, "similarity" and include "identity" differences between sequences which may encode different amino acids that are nevertheless related to each other at the structural, functional, biochemical and/or conformational levels. In a particularly preferred embodiment, nucleotide sequence comparisons are made at the level of identity rather than similarity.

Terms used to describe sequence relationships between two or more polynucleotides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as for example disclosed by Altschul et al. (*Nucl. Acids Res.* 25: 3389, 1997). A detailed discussion of sequence analysis can be found in Unit 19.3 of Ausubel et al. ("Current Protocols in Molecular Biology" John Wiley & Sons Inc, Chapter 15, 1994-1998). A range of other algorithms may be used to compare the nucleotide and amino acid sequences such as but not limited to PILEUP, CLUSTALW, SEQUENCHER or Vector NTI.

The terms "sequence similarity" and "sequence identity" as used herein refers to the extent that sequences are identical or functionally or structurally similar on a nucleotide-by-nucleotide basis over a window of comparison. Thus, a "percentage of sequence identity", for example, is calculated by comparing two optimally aligned sequences over the window of comparison, determining the number of positions at which the identical nucleic acid base (e.g. A, T, C, G, I) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

As detailed above, and more specifically, protein and/or nucleic acid sequence identities (homologies) may be evaluated using any of the variety of sequence comparison algorithms and programs known in the art. The extent of sequence identity (homology) may be determined using any computer program and associated parameters, including those described herein, such as BLAST 2.2.2. or FASTA version 3.0t78, with the default parameters. For example, the sequence comparison algorithm is a BLAST version algorithm. In one aspect, for nucleic acid sequence identity analysis, the BLAST nucleotide parameters comprise word size=11, expect=10, filter low complexity with DUST, cost to open gap=5, cost to extend gap penalty for mismatch=−3, reward for match=1, Dropoff (X) for BLAST extensions in bits=20, final X dropoff value for gapped alignment=50, and all other options are set to default. In one aspect, for polypeptide sequence identity analysis the sequence comparison algorithm is a BLAST version algorithm, e.g., where the BLAST nucleotide parameters comprise word size=3, expect=10, filter low complexity with SEG, cost to open gap=11, cost to extend gap=1, similarity matrix Blosum62, Dropoff (X) for blast extensions in bits=7, X dropoff value for gapped alignment (in bits)=15, final X dropoff value for gapped alignment=25.

Exemplary algorithms and programs include, but are not limited to, TBLASTN, BLASTP, FASTA, TFASTA, and CLUSTALW (Pearson and Lipman, *Proc. Natl. Acad. Sci. USA* 85(8):2444-2448, 1988; Altschul et al., *J. Mol. Biol.* 215(3):403-410, 1990; Thompson et al., *Nucleic Acids Res.* 22(2):4673-4680, 1994; Higgins et al., *Methods Enzymol.* 266:383-402, 1996; Altschul et al., *Nature Genetics* 3:266-272, 1993). Homology or identity can be measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications.

BLAST, BLAST 2.0 and BLAST 2.2.2 algorithms are also used to practice the invention. They are described, e.g., in; Altschul et al. (1990), supra. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighbourhood word score threshold (Altschul et al. (1990) supra). These initial neighbourhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff (1989) *Proc. Natl. Acad. Sci. USA* 89:10915) alignments (B) of 50, expectation (E) of 10, M=5, N=−4, and a comparison of both strands. The BLAST algorithm also performs a statistical analysis of the similarity between two sequences (see, e.g., Karlin & Altschul (1993) *Proc. Natl. Acad. Sci. USA* 90:5873). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001. In one aspect, protein and nucleic acid sequence homologies are evaluated using the Basic Local Alignment Search Tool ("BLAST"). For example, five specific BLAST programs can be used to perform the following task: (1) BLASTP and BLAST3 compare an amino acid query sequence against a protein sequence database; (2) BLASTN compares a nucleotide query sequence against a nucleotide sequence database; (3) BLASTX compares the six-frame conceptual translation products of a query nucleotide sequence (both strands) against a protein sequence database; (4) TBLASTN compares a query protein sequence against a nucleotide sequence database translated in all six reading frames (both strands); and, (5) TBLASTX compares the six-frame translations of a nucleotide query sequence against the six-frame translations of a nucleotide sequence database. The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., *Science* 256:1443-1445, 1992; Henikoff and Henikoff, *Proteins* 17:49-61, 1993). Less preferably, the PAM or PAM250 matrices may also be used (see, e.g., Schwartz and Dayhoff, eds., 1978, Matrices for Detecting Distance Relationships: Atlas of Protein Sequence and Structure, Washington: National Biomedical Research Foundation).

In one aspect of the invention, to determine if a nucleic acid has the requisite sequence identity to be within the scope of the invention, the NCBI BLAST 2.2.2 programs is used, default options to blast. There are about 38 setting options in the BLAST 2.2.2 program. In this exemplary aspect of the invention, all default values are used except for the default filtering setting (i.e., all parameters set to default except filtering which is set to OFF); in its place a "−F F" setting is used, which disables filtering. Use of default filtering often results in Karlin-Altschul violations due to short length of sequence.

The default values used in this exemplary aspect of the invention include:

"Filter for low complexity: ON
Word Size: 3
Matrix: Blosum62
Gap Costs Existence: 11
Extension: 1"

Other default settings are: filter for low complexity OFF, word size of 3 for protein, BLOSUM62 matrix, gap existence penalty of −11 and a gap extension penalty of −1.

The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. For sequence comparison, one sequence can act as a reference sequence to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the numbers of contiguous residues. For example, in alternative aspects of the invention, contiguous residues ranging anywhere from 20 to the full length of an exemplary polypeptide or nucleic acid sequence of the invention are compared to a reference sequence of the same number of contiguous positions after the two sequences are optimally aligned. If the reference sequence has the requisite sequence identity to an exemplary polypeptide or nucleic acid sequence of the invention, that sequence is within the scope of the invention.

The phrase "substantially identical" in the context of two nucleic acids or polypeptides, can refer to two or more sequences that have, e.g., at least about at least 90%, 91%, 92%, 93%, 94%, 95%, 96%, 97%, 98%, 99% or more sequence identity or more nucleotide or amino acid residue (sequence) identity, when compared and aligned for maximum correspondence, as measured using one any known sequence comparison algorithm, as discussed in detail below, or by visual inspection. In alternative aspects, the invention provides nucleic acid and polypeptide sequences having substantial identity to an exemplary sequence of the invention. Nucleic acid sequences of the invention can be substantially identical over the entire length of a polypeptide coding region.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

To determine and identify sequence identities, structural homologies, motifs and the like in silico, the sequence of the invention can be stored, recorded, and manipulated on any medium which can be read and accessed by a computer. Accordingly, the invention provides computers, computer systems, computer readable mediums, computer programs products and the like recorded or stored thereon the nucleic acid and polypeptide sequences of the invention. As used herein, the words "recorded" and "stored" refer to a process for storing information on a computer medium. A skilled artisan can readily adopt any known methods for recording information on a computer readable medium to generate manufactures comprising one or more of the nucleic acid and/or polypeptide sequences of the invention.

Another aspect of the invention is a computer readable medium having recorded thereon at least one nucleic acid and/or polypeptide sequence of the invention. Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

As used herein, the terms "computer," "computer program" and "processor" are used in their broadest general contexts and incorporate all such devices.

The invention provides isolated or recombinant nucleic acids that hybridize under stringent conditions to an exemplary sequence of the invention. In alternative aspects, the stringent conditions are highly stringent conditions, medium stringent conditions or low stringent conditions, as known in the art and as described herein. These methods may be used to isolate nucleic acids of the invention.

In alternative aspects, nucleic acids of the invention as defined by their ability to hybridize under stringent conditions can be between about five residues and the full length of nucleic acid of the invention; e.g., they can be at least 5, 10, 15, 20, 25, 30, 35, 40, 50, 55, 60, 65, 70, 75, 80, 90, 100, 150, 200, 250, 300, 350, 400, 450, 500, 550, 600, 650, 700, 750, 800 or more residues in length, or, the full length of a gene or coding sequence, e.g., cDNA. Nucleic acids shorter than full length are also included. These nucleic acids can be useful as, e.g., hybridization probes, labelling probes, PCR oligonucleotide probes, iRNA, antisense or sequences encoding antibody binding peptides (epitopes), motifs, active sites and the like.

"Hybridization" refers to the process by which a nucleic acid strand joins with a complementary strand through base pairing. Hybridization reactions can be sensitive and selective so that a particular sequence of interest can be identified even in samples in which it is present at low concentrations. Stringent conditions can be defined by, for example, the concentrations of salt or formamide in the prehybridization and hybridization solutions, or by the hybridization temperature, and are well known in the art. For example, stringency can be increased by reducing the concentration of salt, increasing the concentration of formamide, or raising the hybridization temperature, altering the time of hybridization, as described in detail, below. In alternative aspects, nucleic acids of the invention are defined by their ability to hybridize under various stringency conditions (e.g., high, medium, and low), as set forth herein.

Reference herein to a low stringency includes and encompasses from at least about 0 to at least about 15% v/v formamide and from at least about 1 M to at least about 2 M salt for hybridization, and at least about 1 M to at least about 2 M salt for washing conditions. Generally, low stringency is at from about 25-30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m$=69.3+0.41 (G+C) % (Marmur and Doty, *J. Mol. Biol.* 5: 109, 1962). However, the $T_m$ of a duplex DNA decreases by 1° C. with every increase of 1% in the number of mismatch base pairs (Bonner and Laskey, *Eur. J. Biochem.* 46: 83, 1974). Formamide is optional in these hybridization conditions. Accordingly, particularly preferred levels of stringency are defined as follows: low stringency is 6×SSC buffer, 0.1% w/v SDS at 25-42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

Where nucleic acids of the invention are defined by their ability to hybridize under high stringency, these conditions comprise about 50% formamide at about 37° C. to 42° C. In one aspect, nucleic acids of the invention are defined by their ability to hybridize under reduced stringency comprising conditions in about 35% to 25% formamide at about 30° C. to 35° C. Alternatively, nucleic acids of the invention are defined by their ability to hybridize under high stringency comprising conditions at 42° C. in 50% formamide, 5× SSPE, 0.3% SDS, and a repetitive sequence blocking nucleic acid, such as cot-1 or salmon sperm DNA (e.g., 200 n/ml sheared and denatured salmon sperm DNA). In one aspect, nucleic acids of the invention are defined by their ability to hybridize under reduced stringency conditions comprising 35% formamide at a reduced temperature of 35° C.

Following hybridization, the filter may be washed with 6× SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

The temperature range corresponding to a particular level of stringency can be further narrowed by calculating the purine to pyrimidine ratio of the nucleic acid of interest and adjusting the temperature accordingly. Nucleic acids of the invention are also defined by their ability to hybridize under high, medium, and low stringency conditions as set forth in Ausubel and Sambrook. Variations on the above ranges and conditions are well known in the art. Hybridization conditions are discussed further, below.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2× SSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6× SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6× SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

However, the selection of a hybridization format is not critical—it is the stringency of the wash conditions that set forth the conditions which determine whether a nucleic acid is within the scope of the invention. Wash conditions used to identify nucleic acids within the scope of the invention include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2× SSC at a temperature of at least about 50° C. or about 55° C. to about 60° C. for about 15 to about 20 minutes; or, the hybridization complex is washed twice with a solution with a salt concentration of about 2× SSC containing 0.1% SDS at room temperature for 15 minutes and then washed twice by 0.1× SSC containing 0.1% SDS at 68° C. for 15 minutes; or, equivalent conditions. See Sambrook, Tijssen and Ausubel for a description of SSC buffer and equivalent conditions.

In a related embodiment, the present invention provides a method of producing a recombinant avian Type III interferon in a cell comprising the steps of:
(i) introducing into said cell a genetic construct comprising a nucleic acid molecule which encodes or is complementary to a nucleic acid molecule which encodes said avian Type III interferon, placed under the control of a suitable promoter sequence;
(ii) culturing said cell for a time and under conditions sufficient for said nucleic acid molecule to be expressed; and
(iii) isolating said expression product.

In a further related embodiment, the present invention extends to a method of producing an avian Type III interferon fusion molecule in a cell, said method comprising introducing into said cell a genetic construct comprising a nucleic acid molecule which encodes or is complementary to a nucleic acid molecule which encodes an avian Type III interferon polypeptide or a functional fragment, derivative or avian homologue thereof, wherein said polypeptide is a fusion polypeptide between a first Type III interferon and a second Type III interferon or a first Type III interferon and a second Type I or Type II interferon selected from the list comprising IFN-α, IFN-β, IFN-γ, Ch IFN-α, Ch IFN-β, or Ch IFN-γ amongst others.

Accordingly, in yet another related embodiment the present invention extends to a recombinant fusion polypeptide between a first Type III interferon and a second Type III interferon or a first Type III interferon and a second Type I or Type II interferon selected from the list comprising IFN-α, IFN-β, IFN-γ, ChIFN-α, ChIFN-β or ChIFN-γ amongst others.

According to the foregoing embodiments described in this aspect of the invention, the recombinant avian Type III interferon is preferably an avian IFN-λ polypeptide molecule or a fusion molecule comprising same. In a particularly preferred embodiment, the Type III interferon is the ChIFN-λ polypeptide.

In an alternative embodiment, the present invention extends to a genetic construct comprising a nucleic acid molecule as hereinbefore defined or a nucleic acid molecule which encodes or is complementary to a nucleic acid molecule which encodes an avian Type III interferon fusion polypeptide or a functional fragment or derivative thereof, wherein said polypeptide is a fusion polypeptide between a Type III interferon and either a second Type III interferon or a first Type III interferon and a second Type I or Type II interferon selected from the list comprising IFN-α, IFN-β, IFN-γ, Ch IFN-α, Ch IFN-β, or Ch IFN-γ amongst others.

Preferably, said Type III interferon is IFN-λ, in particular ChIFN-λ.

In order to produce a fusion polypeptide, the nucleic acid molecule which encodes a first coding region comprising an avian Type III interferon polypeptide or a functional fragment or derivative thereof is cloned adjacent to a second coding region, optionally separated by a spacer nucleic acid molecule such that the first coding region and the second coding region are in the same open reading frame, with no intervening stop codons between the two coding regions. When translated, the polypeptide thus produced comprises a fusion between the polypeptide products of the first and second coding regions. A genetic construct which encodes a fusion polypeptide further comprises at least one start codon and one stop codon, capable of being recognised by the cell's translational machinery in which expression is intended. Methods for the production of a fusion polypeptide are well-known to those skilled in the art.

Still another aspect of the present invention is directed to antibodies to the protein and nucleic acid molecules hereinbefore defined. Such antibodies may be monoclonal or polyclonal and may be selected from naturally occurring antibodies or may be specifically raised. In the case of the latter, the ChIFNλ polypeptide or nucleic acid antigen may first need to be associated with a carrier molecule to achieve immunogenicity. The antibodies of the present invention are useful as therapeutic or diagnostic agents. An antibody "to" a molecule includes an antibody specific for said molecule.

These antibodies can be used to isolate, identify or quantify a polypeptide of the invention or related polypeptides.

The term "antibody" includes a peptide or polypeptide derived from, modelled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson et al. (1994) *J. Immunol. Methods* 175:267-273; Yarmush et al. (1992) *J. Biochem. Biophys. Methods* 25(4):285-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Single chain antibodies are also included by reference in the term "antibody."

Antibodies to the molecules of the present invention may be monoclonal or polyclonal and may be selected from naturally occurring antibodies or may be specifically raised to these polypeptide and gene products. The present invention extends to recombinant and synthetic antibodies and to antibody hybrids. A "synthetic antibody" is considered herein to include fragments and hybrids of antibodies. The antibodies of this aspect of the present invention are particularly useful for immunotherapy and may also be used as a diagnostic tool or as a means for purifying the subject polypeptide or nucleic acid molecule.

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) *Trends Biotechnol.* 15:62-70; Katz (1997) *Annu. Rev. Biophys. Biomol. Struct.* 26:27-45.

Polyclonal antibodies generated against the polypeptides of the invention can be obtained by direct injection of the polypeptides into an animal or by administering the polypeptides to a non-human animal. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique, the trioma technique, the human B-cell hybridoma technique, and the EBV-hybridoma technique (see, e.g., Cole (1985) in Monoclonal Antibodies and Cancer Therapy, Alan R. Liss, Inc., pp. 77-96).

Techniques described for the production of single chain antibodies (see, e.g., U.S. Pat. No. 4,946,778) can be adapted to produce single chain antibodies to the polypeptides of the invention. Alternatively, transgenic mice may be used to express humanized antibodies to these polypeptides or fragments thereof.

The term "derivative" as used herein includes portions, fragments and parts of the nucleic acid molecule or a translation product thereof. A derivative may also be a single or multiple nucleotide or amino acid substitution, deletion and/or addition. A derivative of the nucleic acid molecule of the present invention also includes nucleic acid molecules capable of hybridising to the nucleotide sequence set forth in SEQ ID NOs: 1 or 3 under at least low stringency conditions. The derivatives of the nucleic acid molecule of the present invention defined herein also includes oligonucleotides, PCR primers, antisense molecules, molecules suitable for use in co-suppression and fusion nucleic acid molecules. Some molecules also contemplated are capable of regulating expression of the ChIFN-λ gene.

Derivatives of the polypeptide molecules defined herein include fragments, parts, portions, mutants, variants and from natural, synthetic or recombinant sources including fusion proteins. The derivatives include fragments having particular epitopes or parts of the entire protein fused to peptides, polypeptides or other proteinaceous or non-proteinaceous molecules. Parts or fragments include, for example, active regions of the ChIFN-λ polypeptide. Derivatives may be derived from insertion, deletion or substitution of amino acids. Conveniently, these are prepared by first making single or multiple nucleotide substitutions, deletions and/or additions to the encoding nucleic acid. Alternatively, once the amino acid sequence is known, amino acids can be chemically added by established techniques and in any sequence required to give the desired mutant. All such derivatives are encompassed by the present invention.

Amino acid insertional derivatives of the avian Type III interferon of the present invention include amino and/or carboxyl terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one residue in the sequence has been removed and a different residue inserted in its place. Typical substitutions are those made in accordance with Table 2.

TABLE 2

Suitable residues for amino acid substitutions

| Original Residue | Exemplary Substitutions |
|---|---|
| Ala | Ser |
| Arg | Lys |
| Asn | Gln; His |
| Asp | Glu |
| Cys | Ser |
| Gln | Asn; Glu |
| Glu | Asp |
| Gly | Pro |
| His | Asn; Gln |
| Ile | Leu; Val |
| Leu | Ile; Val |
| Lys | Arg; Gln; Glu |
| Met | Leu; Ile; Val |
| Phe | Met; Leu; Tyr |
| Ser | Thr |
| Thr | Ser |
| Trp | Tyr |
| Tyr | Trp; Phe |
| Val | Ile; Leu; Met |

Where a derivative avian Type III interferon is produced by amino acid substitution, the amino acids are generally replaced by other amino acids having like properties, such as hydrophobicity, hydrophilicity, electronegativity, bulky side chains and the like. Amino acid substitutions are typically of single residues. Amino acid insertions will usually be in the order of about 1-10 amino acid residues and deletions will range from about 1-20 residues. Preferably, deletions or insertions are made in adjacent pairs, i.e. a deletion of two residues and a corresponding insertion of two residues.

Substitutional amino acid variants are those in which at least one residue in the sequence has been removed and a different residue inserted in its place. An example of substitutional amino acid variants are conservative amino acid substitutions. Conservative amino acid substitutions typically include substitutions within the following groups: glycine and alanine; valine, isoleucine and leucine; aspartic acid and glutamic acid; asparagine and glutamine; serine and threonine; lysine and arginine; and phenylalanine and tyrosine. Additions to amino acid sequences include fusions with other peptides, polypeptides or proteins.

Other examples of recombinant or synthetic mutants and derivatives of the avian Type III interferon polypeptide of the present invention include single or multiple substitutions, deletions and/or additions of any molecule associated with the polypeptide such as carbohydrates, lipids and/or proteins or polypeptides.

For convenience and by way of shorthand notation, reference herein to an avian Type III interferon such as IFN-λ, ChIFN-λ or an avian interferon-like polypeptide includes reference to any derivatives thereof as contemplated above.

Reference to "fragments" includes reference to parts and portions, from natural, synthetic or recombinant sources including fusion proteins. Parts or fragments include, for example, active regions of ChIFNλ.

As used herein, "avian homologues" of a nucleotide sequence shall be taken to refer to an isolated nucleic acid molecule which is substantially the same as the nucleic acid molecule of the present invention or its complementary nucleotide sequence, notwithstanding the occurrence within said sequence, of one or more nucleotide substitutions, insertions, deletions, or rearrangements. Homologues also should be understood as a reference to nucleic acid or protein molecules isolated from or otherwise corresponding to molecules found in avian species other than the chicken. A "homologue" refers to a sequence (nucleotide or protein) in another prokaryotic organism which exhibits at least about 60% and preferably 65%, 70%, 75%, 80%, 85%, 90%, 91%, 92%, 93%, 94%, 95%, 96%, 97%, 98% or 99% identity to the reference sequences.

Reference to a "functional" fragment, derivative or avian homologue thereof, should be understood as a reference to a molecule which is capable of performing one or more of the activities of an avian IFN-λ as hereinbefore defined. More particularly, reference to a functional fragment, derivative or avian homologue thereof shall be taken to refer to a polypeptide, protein or other substance which is capable of inducing or modulating an immune response in an avian species to an antigen or infectious agent such as, but not limited to infectious bronchitis virus, avian infectious laryngeotracheitis virus, infectious bronchitis virus, Newcastle disease virus, Marek's Disease virus, chicken anemia virus, avian influenza virus, *E. coli*, *Salmonella* ssp., *Eimeria* ssp. or *Mycoplasma* ssp. amongst others.

Yet another aspect of the present invention provides a method for identifying an avian Type III interferon genetic sequence, or a functional fragment or derivative thereof.

In one embodiment, said method comprises contacting a nucleic acid sample with a hybridisation effective amount of a Type III interferon probe and then detecting said hybridisation.

Said nucleic acid sample may comprise, for example, genomic DNA, mRNA or cDNA.

The genetic sequence of interest may be in a recombinant form, in a virus particle, bacteriophage particle, yeast cell, animal cell, or a plant cell. Preferably, the genetic sequence originates from an avian species. More preferably, the genetic sequence originates from an avian species selected from the list comprising chickens, turkeys, bantams, quails, guinea fowl, ducks, geese, ostriches, emus, pigeons, canaries, budgerigars, parrots and finches, amongst others. In a particularly preferred embodiment the genetic sequences originate from chickens.

Preferably, the avian Type III interferon probe comprises a sequence of nucleotides of at least 10, 20, 30, 40 or 50 nucleotides, although the use of larger probes are also contemplated in the present invention, derived from or directed to the nucleotide sequence set forth in SEQ ID NO: 1 or 3 or its complement or a functional fragment or derivative thereof. Preferably, this sequence is labelled with a reporter molecule capable of giving an identifiable signal (e.g. a radioisotope such as P or S or a biotinylated molecule).

An alternative embodiment of the present invention provides a method for identifying an avian Type III interferon genetic sequence or a functional fragment or derivative thereof comprising contacting two non-complementary nucleic acid "primer molecules" of at least 12 nucleotides in length derived from the nucleotide sequence of an avian Type III cytokine gene with a nucleic acid template molecule comprising nucleotide sequences related to the primer molecule sequences and amplifying specific nucleic acid molecule copies of the template molecule in an amplification reaction.

In one example, the first primer molecule is preferably directed to the sense strand of an avian IFN-λ gene such as the ChIFN-λ gene and in particular from the nucleotide sequence set forth in SEQ ID NOs:1 or 3 or a homologue or derivative thereof and the second primer molecule is preferably directed to the antisense strand of an avian IFN-λ gene such as the ChIFN-λ gene and in particular from the complement of the nucleotide sequence set forth in SEQ ID NOs:1 or 3 or a homologue or derivative thereof. Accordingly, both primers hybridise to said template molecule such that, in the presence of a DNA polymerase enzyme, a cofactor and appropriate substrate, DNA synthesis occurs in the 5' to 3' direction from each primer molecule towards the position on the DNA where the other primer molecule is hybridised, thereby amplifying the intervening DNA.

The nucleic acid primer molecule may further consist of a combination of any of the nucleotides adenine, cytosine, guanine, thymidine, or inosine, or functional analogues or derivatives thereof, capable of being incorporated into a polynucleotide molecule provided that it is capable of hybridising under at least low stringency conditions to the nucleic acid molecule set forth in SEQ ID NOs:1 or 3.

The nucleic acid primer molecules may further be each contained in an aqueous pool comprising other nucleic acid primer molecules. More preferably, the nucleic acid primer molecule is in a substantially pure form.

The nucleic acid template molecule may be in a recombinant form, in a virus particle, bacteriophage particle, yeast cell, animal cell, or a plant cell. Preferably, the related genetic sequence originates from an avian cell, tissue, or organ. More preferably, the related genetic sequence originates from a chicken cell, tissue or organ.

As would be familiar to the skilled artisan, the expression of a gene, or the modulation of expression of a target gene in vitro can be determined by measuring changes in the levels of the expression product of said gene.

Accordingly, in another embodiment the invention provides a method for detecting the presence of an avian Type III interferon polypeptide or a functional fragment, derivative or homologue thereof.

A variety of methods well known in the art can be used to determine polypeptide levels either directly or indirectly. Such methods include immunochemical methods, such as western blotting, ELISA, immunoprecipitation, and RIA, gel electrophoresis methods including one and two-dimensional gels, methods based on protein or peptide chromatographic separation, methods that use protein-fusion reporter constructs and colorimetric readouts, methods based on characterization of activity translated polysomal mRNA, and mass spectrometric detection.

In practicing the screening methods of the invention, a test compound can be contacted with a polypeptide of the invention in vitro or administered to a cell of the invention or an avian species in vivo. Without limiting the present invention to any one theory or mode of action a reference to a test compound includes reference to an immunointeractive molecule such as an 'antibody' as hereinbefore defined.

Immunoassays are useful in detecting the presence of a cytokine in an avian species, in particular to detect an immune response in which the level of said avian cytokine is altered, for example following infection with a pathogen. As a consequence, such an immunoassay is of particular use in determining whether an avian has been exposed to a pathogen or is currently infected with a pathogen or has a prolonged low-grade pathogenic infection. Immunoassays are also useful for the quantitation of cytokines, in particular for screening genetic stocks for high cytokine-expressing lines with improved disease-resistance to a pathogen. The invention described herein extends to all such uses of immunointeractive molecules and diagnostic assays which require said immunoassays for their performance.

A wide range of immunoassay techniques may be such as those described in U.S. Pat. Nos. 4,016,043, 4,424,279 and 4,018,653. These methods may be employed for detecting a Type III interferon. By way of example only, an antibody raised against ChIFN-λ is immobilised onto a solid substrate to form a first complex and a biological sample from an animal to be tested for the presence of cytokine brought into contact with the bound molecule. After a suitable period of incubation, for a period of time sufficient to allow formation of an antibody-cytokine secondary complex, a second ChIFN-λ antibody labelled with a reporter molecule capable of producing a detectable signal is then added and incubated, allowing sufficient time for the formation of a tertiary complex of antibody-cytokine-labelled antibody. Any unreacted material is washed away, and the presence of the tertiary complex is determined by observation of a signal produced by the reporter molecule. The results may either be qualitative, by simple observation of the visible signal or may be quantitated by comparison with a control sample containing known amounts of hapten. Variations of this assay include a simultaneous assay, in which both sample and labelled antibody are added simultaneously to the bound antibody, or a reverse assay in which the labelled antibody and sample to be tested are first combined, incubated and then added simultaneously to the bound antibody. These techniques are well known to those skilled in the art, and the possibility of minor variations will be readily apparent. The antibodies used above may be monoclonal or polyclonal.

The solid substrate is typically glass or a polymer, the most commonly used polymers being cellulose, polyacrylamide, nylon, polystyrene, polyvinyl chloride or polypropylene. The solid supports may be in the form of tubes, beads, discs or microplates, or any other surface suitable for conducting an immunoassay. The binding processes are well-known in the art and generally consist of cross-linking covalently binding or physically adsorbing the molecule to the insoluble carrier.

By "reporter molecule", as used in the present specification, is meant a molecule which, by its chemical nature, produces an analytically identifiable signal which allows the detection of antigen-bound antibody. Detection may be either qualitative or quantitative. The most commonly used reporter molecule in this type of assay are either enzymes, fluorophores or radionuclide containing molecules (i.e. radioisotopes). In the case of an enzyme immunoassay, an enzyme is conjugated to the second antibody, generally by means of glutaraldehyde or periodate. As will be readily recognised, however, a wide variety of different conjugation techniques exist which are readily available to one skilled in the art. Commonly used enzymes include horseradish peroxidase, glucose oxidase, β-galactosidase and alkaline phosphatase, amongst others. The substrates to be used with the specific enzymes are generally chosen for the production, upon hydrolysis by the corresponding enzyme, of a detectable colour change. It is also possible to employ fluorogenic substrates, which yield a fluorescent product.

Alternatively, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. As in the EIA, the fluorescent labelled antibody is allowed to bind to the first antibody-hapten complex. After washing off the unbound reagent, the remaining complex is then exposed to the light of the appropriate wavelength, the fluorescence observed indicates the presence of the hapten of interest. Immunofluorescence and EIA techniques are both very well established in the art and are particularly preferred for the present method. However, other reporter molecules, such as radioisotope, chemiluminescent or bioluminescent molecules, may also be employed. It will be readily apparent to the skilled technician how to vary the procedure to suit the required purpose.

An antibody as hereinbefore defined is also useful in purifying the recombinant avian cytokine of the present invention. Methods for the affinity purification of proteins using antibodies are well-known to those skilled in the art.

The identification and sequencing of the avian Type III IFN disclosed herein now facilitates the development of a range of diagnostic and prophylactic/therapeutic treatment protocols for use with respect to avian disease conditions. Also facilitated is the development of reagents for use therein. Accordingly, the present invention should be understood to extend to the use of the avian Type III Interferon polypeptide disclosed herein or a functional fragment, derivative, or homologue thereof in the therapeutic and/or prophylactic treatment of aves.

For example, the present invention is particularly useful, but in no way limited to, use in therapeutically or prophylactically treating avian species infected with a pathogenic organism. However, it should be understood that reference to prophylactic treatment as described herein also extends to the prophylaxis or treatment of healthy avians so as to provide protection against infection or other advantageous outcome.

Accordingly, in one aspect there is provided a method for inducing or upregulating an immune response in an aves, said method comprising administering to said aves an effective amount of a polypeptide or nucleic acid molecule as hereinbefore defined for a time and under conditions sufficient to induce, enhance or otherwise maintain an immune response.

In another aspect of the present invention there is provided a method of treatment or prophylaxis of an aves said method comprising administering to said aves an effective amount of an avian Type III interferon polypeptide or nucleic acid molecule as hereinbefore defined or a functional fragment, derivative or homologue thereof for a time and under conditions sufficient to maintain, stimulate or enhance the immunoresponsiveness of said aves.

In a further aspect of the present invention there is provided a method of treatment or prophylaxis of an aves, which aves has been exposed to or infected with a pathogenic organism, said method comprising administering to said aves an effective amount of an avian Type III interferon polypeptide or nucleic acid molecule as hereinbefore defined or a functional fragment, derivative, or homologue thereof.

In a preferred embodiment of the present invention said aves include poultry, domestic birds or game birds.

The term "aves" as used herein extends to chickens, turkeys, bantams, quails, guinea fowl, ducks, geese, ostriches, emus, pigeons, canaries, budgerigars, parrots and finches, amongst others. Particularly preferred aves are poultry, domestic bird or game birds and, more preferably chickens.

According to the foregoing embodiment, it is particularly preferred that said avian cytokine is a Type III interferon molecule, in particular IFN-λ.

In a most particularly preferred embodiment, said avian cytokine is ChIFN-λ.

The present invention is of particular use in the treatment or prophylaxis of aves, against infection by pathogens such as bacteria, viruses or parasites. Examples of such pathogens includes avian influenza, infectious bursal disease virus, avian infectious bronchitis virus, avian infectious laryngeotracheitis virus, infectious bronchitis virus, Newcastle disease virus, Marek's Disease virus, chicken anemia virus, avian influenza virus, *E. coli, Salmonella* ssp., *Eimeria* ssp. or *Mycoplasma* ssp. amongst others.

Reference herein to "treatment" and "prophylaxis" is to be considered in its broadest context. The term "treatment" does not necessarily imply that a mammal is treated until total recovery. Similarly, "prophylaxis" does not necessarily mean that the subject will not eventually contract a disease condition. Accordingly, treatment and prophylaxis including amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition.

An "effective amount" means an amount necessary at least partly to attain the desired response, or to delay the onset or inhibit progression or halt altogether, the onset or progression of a particular condition of the individual to be treated, the taxonomic group of individual to be treated, the degree of protection desired, the formulation of the vaccine, the assessment of the medical situation, and other relevant factors. It is expected that the amount will fall in a relatively broad range that can be determined through routine trials.

In an alternative embodiment, the present invention provides a method of treatment or prophylaxis of an aves exposed to or infected with a pathogenic organism, said method comprising administering to said aves an effective amount of a first avian cytokine comprising a Type III interferon in combination with a second avian cytokine molecule, for a time in combination and under conditions sufficient to maintain, stimulate or enhance the immunoresponsiveness of said animal.

Said first and second cytokines may be co-administered as two molecules or they may be administered as a fusion molecule. Preferably, said second avian cytokine is selected from Type I or Type II interferons such as, but not limited to, IFN-α, IFN-β, IFN-γ, Ch IFN-α, Ch IFN-β, or Ch IFN-γ amongst others or a Type III interferon or any other avian cytokine.

In a most preferred embodiment, said first avian cytokine and said second avian cytokine are a fusion molecule.

According to this embodiment of the invention, the first and second avian cytokines interact with the immune system of an animal to stimulate, enhance or otherwise modulate the immunoresponsiveness of the immune system against pathogen attack.

A further aspect of the present invention relates to avian interferon III polypeptide or encoding nucleic acid molecule for use in therapy or prophylaxis of an aves.

A still further aspect of the present invention relates to the use of an avian Type III interferon polypeptide or nucleic acid molecule in the manufacture of a medicament for the modulation of an immune response in an aves and/or for the treatment or prophylaxis of an ayes.

Preferably, said avian Type III interferon molecule is IFN-λ, in particular ChIFN-λ.

Type III IFN of the present invention may be administered throughout the life cycle of a bird for which treatment or prophylaxis is indicated. The developmental stage of the bird during which treatment or prophylaxis is most effective will vary depending upon the nature of the pathogen against which protection is sought, including its mode of transmission and period of highest infectivity. By "period of highest infectivity" is meant the developmental stage of the host during which it is most vulnerable to attack by a particular pathogen and or during which there is a greater probability of incurring livestock losses or reduced productivity as a result of the pathogen infection. The parameters affecting optimum developmental stages of animals for administration of the subject cytokines will be well-known to those skilled in the art.

Accordingly, the method of treatment or prophylaxis of the present invention extends to administration of the subject avian cytokine at any developmental stage in the life cycle of poultry, domestic or game birds for which treatment or prophylaxis is indicated.

The cytokine or nucleic acid molecule of the invention may be administered by any means including for example, by injection either in ovo or post-hatching by injection such as intra-peritoneal, intra-dermal, intra-muscular, intra-ocular, intra-venous, sub-cutaneous or other injection means, by ingestion as a medicated foodstuff or therapeutic foodstuff or by introducing to said avian an isolated nucleic acid molecule which encodes or is complementary to a nucleic acid molecule which encodes said cytokine or, alternatively, a vector comprising a genetic construct capable of expressing said cytokine in vivo or in ovo, for example a live recombinant viral vector, live recombinant bacterial vector.

Where the cytokine of the invention is administered via the introduction of an isolated nucleic acid molecule encoding said cytokine, such as a DNA or RNA molecule, or a vector comprising a genetic construct capable of expressing said cytokine, the nucleic acid molecule or genetic construct must be transcribed and translated to produce the biologically-active cytokine molecule following its administration to an appropriate avian subject.

Another important application of the cytokines of the present invention is as natural adjuvants for vaccines, particularly for subunit or synthetic peptide vaccines produced by recombinant DNA technology.

The term "adjuvant" as used herein shall be taken to mean a substance that, when administered to an animal in combination with a second substance or antigen, enhances the production of immunointeractive molecules, such as antibodies, which recognise the second substance or antigen molecule. An adjuvant may be used therapeutically to produce antibodies against small amounts of antigen or to prolong the period of antibody production or to increase the amount of antibody produced. Whilst not wishing to be bound by any theory or mode of action, adjuvants work by inducing a local influx of antibody-forming cells to the site of administration.

Accordingly, a further aspect of the present invention provides an adjuvant comprising an avian cytokine molecule, wherein said cytokine is a Type III interferon or a fusion molecule between said Type III interferon molecule and a second cytokine molecule and optionally, a pharmaceutically-acceptable carrier, excipient or diluent.

Preferably, said avian Type III interferon molecule is IFN-λ, in particular ChIFN-λ.

Where said avian cytokine is a fusion molecule, said second cytokine may be any cytokine molecule which is functional in avian species, in particular IFN-α, IFN-β, IFN-γ, Ch INF-α, Ch IFN-β, or Ch IFN-γ or a Type III interferon molecule or any other cytokine.

In accordance with the present invention, an avian cytokine such as a Type III interferon, in particular ChIFN-λ, is used in vaccines to enhance the immunogenicity of antigens, particularly in subunit vaccines, leading to increased antibody titre in individual birds, increased protection of birds that are immunised against a specific antigen (i.e. enhanced flock immunity) and/or increased persistence of protective antibodies in immunised birds. A further advantage provided by the present invention is a reduction in the quantity of specific antigen required to effectively immunise animals, thereby leading to reduced production costs.

The cytokine or vaccine of the invention described according to these embodiments may be administered by any means including for example, by injection either in ovo or post-hatching by injection such as intra-peritoneal, intra-dermal, intra-muscular, intra-ocular, intra-venous, sub-cutaneous or other injection means, by ingestion as a medicated foodstuff or therapeutic foodstuff.

Advances in slow-release technology and the development of live non-pathogenic bacteria and viruses as delivery vectors for these molecules will ensure their cost-effectiveness when administered to poultry, domestic birds or game birds. They may also be used in nucleic acid vaccination. Accordingly, the avian cytokine or vaccine of the present invention may also be delivered by genetic means. For example, recombinant avian ChIFN-λ may be encoded by a genetic construct present in a delivery system such as a virus, yeast, bacterium, protozoan, insect, avian or mammalian cell. The expression of such a delivery system in a target animal will enable delivery of the recombinant avian cytokine.

According to this embodiment, there is contemplated a genetic construct comprising: (i) a first nucleotide sequence encoding an avian Type III interferon or a fusion cytokine molecule between said Type III interferon and a second cytokine, placed operably under the control of a first promoter sequence; (ii) a second nucleotide sequence defining an antigen against which immunisation is required, placed operably under the control of a second promoter sequence; and (iii) a delivery vehicle comprising genetic sequences which facilitate replication of said genetic construct in a delivery cell such as a bacterial, yeast, insect, a protozoan animal or a mammalian cell.

Preferably, said Type III interferon is IFN-λ, in particular ChIFN-λ. It is also preferred that said second cytokine be selected from the list comprising IFN-α, IFN-β, IFN-γ, Ch IFN-α, Ch IFN-β, or Ch IFN-γ or, alternatively, a Type III interferon or any other cytokine.

According to this embodiment, the delivery vehicle would not in normal use be harmful or pathogenic to the target animal. Conveniently, attenuated delivery vehicles are employed. Particularly useful delivery vehicles are vectors such as attenuated viruses and recombinant viral and bacterial vectors.

For example, an attenuated viral vector is used as a live vaccine. The genetic sequence encoding an avian cytokine such as ChIFN-λ or a derivative thereof is cloned into the viral sequence and the recombinant virus used to infect target animals. The recombinant virus causes infection and replicates in the animal cells resulting in production of the recombinant cytokine. The infecting recombinant virus may subsequently be eliminated after production of an immunomodulatingly effective amount of the recombinant cytokine. A similar protocol is adopted with live bacterial carriers. Alternatively, a non-replicating, non-infectious viral vector may be used. A non-replicating viral vector provides a means of introducing a genetic sequence which is transiently capable of expression of the desired cytokine because the non-replicating viral vector is not capable of cell-to-cell transmission.

The present invention provides an opportunity to enhance an immune response in animals and in particular poultry, domestic birds or game birds (such as those described above) by the administration of an avian cytokine, in particular a Type III interferon such as ChIFN-λ or a derivative thereof, either directly or via the expression of recombinant genetic sequences. This is of particular importance since most subunit and synthetic peptide vaccines are only weakly antigenic. The administration of the cytokines may be alone, in combination with an antigen or as a fusion molecule. Administration may be via an attenuated virus, recombinant viral vector or bacterial vector or may be by administration of the cytokine by, for example, injection or oral ingestion (e.g. in medicated foodstuff).

The present invention extends to a veterinary pharmaceutical composition for use in avian species, for example poultry, domestic bird or game birds such as to enhance the immune system or improve its immunocompetence or to facilitate immunomodulation in said birds, said composition comprising a recombinant avian Type III interferon or a fusion molecule between a Type III interferon and a second cytokine fused to an antigen or genetic sequences encoding same and one or more carriers and/or diluents acceptable for veterinary use.

Preferably, where the composition comprises a recombinant avian cytokine as hereinbefore defined, the composition is injected in ovo or post-hatching, or administered via aerosol or ingestion. Where the composition comprises genetic material, it is administered as part of a viral vector, bacterial vector or as a nucleic acid molecule.

Conditions in poultry, domestic bird or game birds for which treatment might be required include infectious disease induced by any viral, bacterial or parasitic agent such as those discussed earlier, cancer, immunosuppression, allergy and to enhance or suppress reproductive systems. Conditions would also include situations where animals are in an immunocompromised state such as during or following stress, due to overcrowding and transport process, changes in climate.

Molecules of the present invention may be used in a homologous sense in that they are derived from the same species, or they may be used in a heterologous sense where the avian Type III interferon is effective in an avian species other than the species from which it has been derived. The compositions may also contain other active molecules such as antibiotics or antigen molecules. Combinations of cytokine molecules with antigen molecules may increase the efficacy of vaccines.

The present invention, therefore, extends to a veterinary pharmaceutical composition comprising an immunomodulatory effective amount of an avian Type III interferon or a fusion molecule between an avian Type III interferon and a second cytokine or a genetic sequence capable of expressing same and one or more carriers and/or diluents acceptable for veterinary use.

In a preferred embodiment, said Type III interferon is IFN-λ, in particular ChIFN-λ.

Where said pharmaceutical composition comprises a fusion molecule, said fusion is preferably a fusion between ChIFN-λ or a functional fragment, derivative or homologue thereof and a second cytokine selected from the list comprising Type I interferons such as IFN-α, IFN-β, ChIFN-α, ChIFN-β, Type II interferons, such as IRN-α or a Type III interferon or any other cytokine.

The active ingredient(s) of the pharmaceutical composition is/are contemplated to exhibit activity in stimulating, enhancing or otherwise facilitating an immune response in an animal species and in particular a poultry, domestic bird or game bird when administered in an amount which depends on the particular case. The variation depends, for example, on the cytokine and, in some cases, the antigen involved in stimulating the immune response. For example, from about 0.5 µg to about 20 mg of a particular cytokine which may be combined with other cytokines, per kilogram of body weight per day may be required. Dosage regimen may be adjusted to provide the optimum therapeutic response. For example, several divided doses may be administered in one or more of daily, weekly or monthly or in other suitable time intervals or the dose may be proportionally reduced as indicated by the exigencies of the situation. The active compound may be administered by injection either in ovo or post-hatching or by oral ingestion in any convenient manner or may be administered via a genetic sequence si-ch as in a viral or bacterial vector.

The active compounds may also be administered in dispersions prepared in glycerol, liquid polyethylene glycols, and/or mixtures thereof and in oils. Under ordinary conditions of storage and use, these preparations contain a preservative to prevent the growth of microorganisms.

The pharmaceutical forms suitable for parenteral administration include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, antibiotics, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example.

Sterile injectable solutions are prepared by incorporating the active compounds in the required amount in the appropriate solvent with various of the other ingredients enumerated above, as required, followed by filter sterilisation. Generally, dispersions are prepared by incorporating the various sterilised active ingredient(s) into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Carriers and/or diluents suitable for veterinary use include any and all solvents, dispersion media, aqueous solutions, coatings, antibacterial and antifungal agents, isotonic and absorption delaying agents, and the like. The use of such media and agents for pharmaceutically active substances is well known in the art. Except insofar as any conventional media or agent is incompatible with the active ingredient, use thereof in the composition is contemplated. Supplementary active ingredients can also be incorporated into the compositions. The latter is particularly contemplated as far as the present invention extends to multivalent vaccines or multi-component cytokine molecules.

The pharmaceutical veterinary compositions of the present invention may comprise in addition to an avian Type III interferon or a fusion molecule comprising same, one or more other active compounds such as antigens and or immune stimulating compounds.

The cytokine may also be delivered by a live delivery system such as using a bacterial expression system to express the cytokine protein in bacteria which can be incorporated into gut flora. Alternatively, a viral expression system can be employed or incorporated into a recombinant vaccine. In this regard, one form of viral expression is the administration of a live vector generally by spray, feed or water where an infecting effective amount of the live vector (e.g. virus or bacterium) is provided to the animal. Another form of viral expression system is a non-replicating virus vector which is capable of infecting a cell but not replicating therein. The non-replicating viral vector provides a means of introducing genetic material for transient expression into a cytokine. The mode of administering such a vector is the same as a live viral vector.

The present invention is further described by reference to the following non-limiting Figures and Examples.

EXAMPLE 1

Cloning, Expression and Characterization of a Chicken Type III IFN

Material and Methods
Isolation of Lymphocytes and Cell Culture

Spleens were harvested from 4 week old specific pathogen free chickens (SPF) chickens, and single cell suspensions of leukocytes were prepared from individual spleens by dispersal through a 70 µm strainer in to Petri dishes containing DMEM. Suspensions were layered over lymphoprep (Nicomed Pharma AS, Oslo) and centrifuged at 1500 $g_{max}$ for 15 min. Mononuclear cells at the interface were collected, washed, resuspended and cultured in DMEM supplemented with 10% FCS. The continuous chicken macrophage-like cell line HD11 was maintained in RPMI supplemented with 6% FCS, 2 mM glutamine, penicillin (100 U/ml) and streptomycin (100 µg/ml). HD11 cells were passaged as required and seeded overnight to 80% confluence prior to IFN treatments.
Reagents The synthetic dsRNA analog, Poly (I:C) (Invivogen), and the ssRNA analog poly C (Invivogen), were prepared and stored as per manufacturers instructions. Both chicken IL6 (chIL6) (Asif et al., manuscript in preparation) and ChIFNγ (ChIFNγ) (Digby and Lowenthal 1995) were produced in our laboratory. Nucleic acid was stored at −80° C. and cytokines were stored at 4° C.
Virus Culture The influenza virus A/PR/8/34 (PR8) (Talon et al., 2000), a H1N1 type, was cultured for 48 h in the allantoic cavity of 10-day old embryonated chicken eggs. The virus containing allantoic fluid was then harvested and aliquoted and stored at −80° C. The virus was subsequently passaged 5 times in HD11 chicken macrophages and infectivity was titered on monolayers of these cells by determining the 50% endpoint of tissue culture infective dose ($TCID_{50}$).
RNA Isolation Reverse Transcription RNA was harvested using Tri-reagent (Sigma-Aldrich) according to the manufacturer's instructions. Extracted RNA was subjected to DNase treatment using a DNase 1 (Sigma-Aldrich) according to the manufacturer's instructions. The DNase treated RNA was then reverse-transcribed to complimentary DNA (cDNA) using a reverse transcription kit (Promega).
Cloning and Expression IFN-specific primers were designed to amplify full length ChIFNλ, ChIFNα, and ChIFNβ and are provided in Table 3. Synthesised cDNA was used with gene specific primers in a standard PCR amplification performed using 35 cycles of 94° C. for 1 min, 55° C. for 1 min and 72° C. for 1 min with a further 15 min extension at 72° C. following the last cycle. DNA products of interest were gel purified using a gel extraction kit (Qiagen) and then ligated into pGEM®T-Easy (Promega) for sequence analyses. These vectors were designated pGemIFNλ, pGemIFNα and pGemIFNβ.
Construction of pQE50IFNλ, pQE50IFNα and pET32IFNβ Expression Vectors The primers λ3 and λ4 (Table 3) contained a BamHI and HindIII restriction site, respectively, and were used to amplify the ChIFNλ mature ORF from pGemIFNλ in a standard PCR. The PCR fragment was purified and restriction digested and then ligated downstream of the 6× His-tag sequence of BamHI and HindIII restriction digested pQE50 (Qiagen) expression vector to generate pQE50IFNλ. ChIFNα was subcloned similarly into the expression vector pQE30 (Qiagen) using the primers α3 and α4 (Table 3) to generate pQE30IFNα. ChIFNβ was also similarly subcloned into the expression vector pET32 (Novagen) using the primers β3 and β4 (Table 3) to generate pET32IFNβ. Restriction digestions using BamHI and HindIII as well as DNA sequencing were used to confirm all three expression vectors.
Expression and Purification of Recombinant ChIFNλ, α and β

Each of the chicken IFN were expressed using standard expression procedures (Qiagen, 1997). Cultures of E. coli strain TOP10F'(pQE30IFNα), TOP10F'(pET32IFNβ) or TOP10F'(pQE50IFNλ) were cultured and induced by isopropyl β-D-thiogalactoside (IPTG) then harvested by centrifugation. Sonicated cell lysates were treated with Triton X-100 and protein was immobilised using metal-affinity chromatography then eluted with imidazole. Samples for analyses were collected at each purification step and run on a 12% SDS-PAGE gel. Samples were detoxified using Detoxi-gel (Pierce, USA) to remove any LPS from purified samples.
IFN Activity Using Semliki Forest Virus (SFV) Bioassay IFN activity was determined by its capacity to inhibit the effects of SFV-mediated cytolysis as previously described (Lowenthal et al., 1995). Chicken embryonic fibroblasts (CEF) were seeded into 96-well plates at a rate of $5 \times 10^4$ cells/well and incubated at 37° C. overnight in DMEM supplemented with 10% FCS. Media was then discarded and samples were added in duplicate. Cells were incubated with samples for 18 h and then media was replaced with 100 μl of DMEM containing SFV ($10^3$ $TCID_{50}$/ml) and incubated overnight at 37° C. Cell viability was determined by the uptake of neutral red dye and absorbance ($OD_{540}$) measured.

Nitrate Production Assay

The chicken cell line (HD11) was used to determine nitric oxide production by measuring the accumulation of nitrite (Green et al., 1982; Sung et al., 1991) as determined by the Greiss assay (Migliorini et al., 1991) and then measuring the absorbance ($OD_{540}$).

IFN Activity Determined by PR8 Inhibition

HD11 cells were grown to 80% confluence and IFN was then added. PR8 was added to RPMI containing trypsin (5 μg/ml) then added to wells (moi 0.1) and incubated for 1 h. Media containing virus was then replaced with RPMI supplemented with 1% FCS and 5 μg/ml trypsin and incubated at 37° C. for up to 90 h. Supernatant was then tested for the presence of virus by hemagglutination activity.

Hemagglutination Assay

The hemagglutination (HA) assay was carried out in microtiter plates (Thermo). Serial 2-fold dilutions of the virus samples in PBS were combined with an equal volume of 0.5% (vol/vol) suspended fresh chicken erythrocytes harvested from SPF chickens. The combined virus and erythrocytes were allowed to incubate at RT for 30 min. Wells that contained an adherent homogenous layer of erythrocytes were observed as agglutinated and scored as positive. The lowest virus dilution that displayed positive agglutination was recorded as HA units per ml (HAU) (Li et al., 2005).

Semi-quantitative RTPCR (qRT-PCR)

The relative quantitation of gene expression following treatment was carried out on an ABI Prism 7700 sequence detection system and used the comparative threshold cycle (Ct) method, to derive fold change gene expression, according to the manufacturers instructions (Applied Biosystems). Relative gene expression was calculated using the mean values obtained with the arithmetic formula ΔΔCt (Applied Biosystems) as previously described (Karpala et al., in press).

Results

Molecular Cloning and Bioinformatic Analyses of ChIFNλ cDNA derived from chicken splenic leukocytes stimulated with Poly (I:C) for 2 h was used as a template for PCR amplification of chicken IFNλ. A band of 561 basepairs (bp) was identified (data not shown). DNA bands of 582 and 612 bp were similarly obtained for cloning of ChIFNα and ChIFNβ respectively, (data not shown). The sequence of all 3 IFN were obtained. ChIFN α and β sequences have previously been described (Sekellick et al., 1994). Hence the newly identified chicken gene was termed ChIFNλ. The genomic structure of ChIFNλ appeared to be organized into 5 exonic regions and yielded a predicted protein of 186 aa with a molecular weight of 21 kDa (FIG. 3). Signal peptide analyses (Bendtsen et al., 2004) of ChIFNλ revealed a cleavage site between residues 21 and 22 (FIG. 3). ChIFNλ has relatively high amino acid (aa) identity to HuIFNλII (36%) whereas relatively lower aa identity was seen compared with other chicken cytokines (Table 4). The translated ChIFNλ was compared to several other previously defined IFNλII and conserved residues were identified (FIG. 2).

Figure 4:
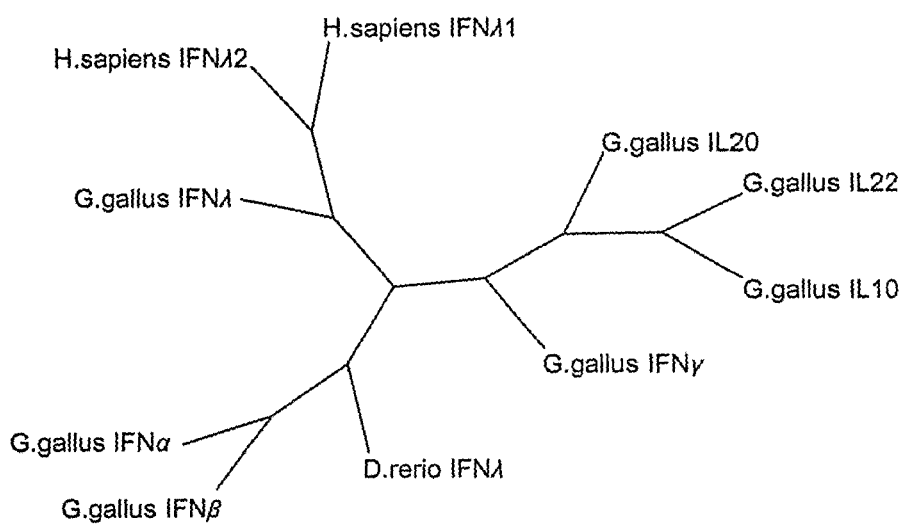
FIG. 4 is a schematic representation of an unrooted phylogenetic tree showing the relationship of the amino acid sequence of ChIFNλ, several other vertebrate IFNλ and selected other chicken cytokines using the complete coding sequence. The Genebank accession no for each gene can be found in Table 4.

Phylogenetic analyses further showed that ChIFNλ clusters near HuIFNλII (IL28A) and supported ChIFNλ as most structurally similar to HuIFNλ2 (FIG. 4).

Expression of Recombinant ChIFNα, β and λ

Figure 5:
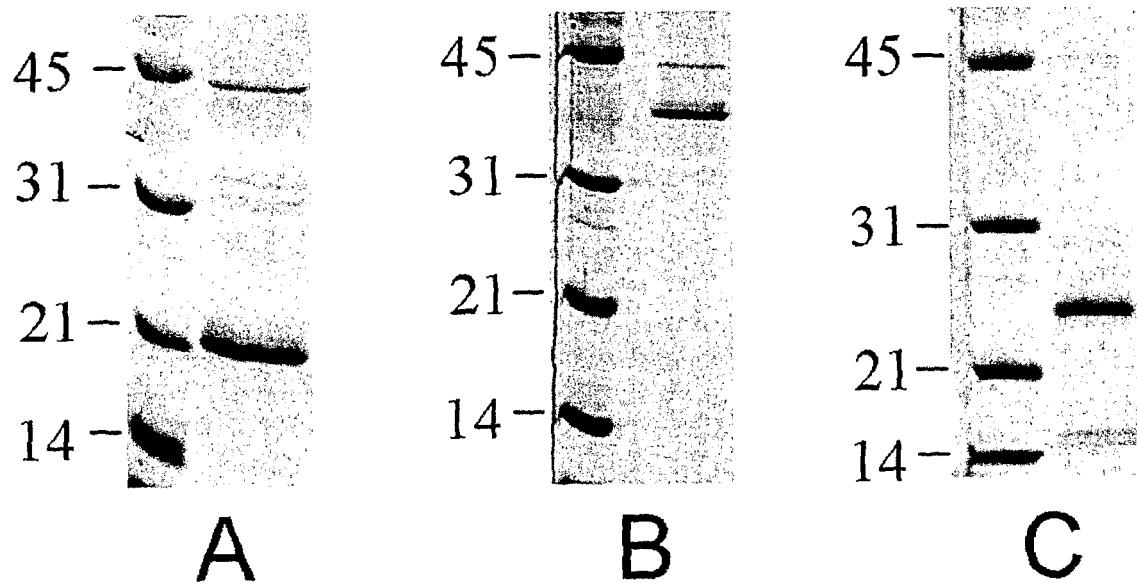
FIG. 5 is an image of SDS-PAGE analyses of *E. coli* expressed recombinant chicken IFN. *E. coli* expressed recombinant ChIFNα, ChIFNβ and ChIFNλ proteins were purified by Ni-NTA metal-affinity chromatography following IPTG induction. These recombinant proteins were then run on a 12% SDS-PAGE and analysed by Coomassie Brilliant blue staining. Broad range molecular weight markers (Markers) were included for reference.

The ORF coding for the mature protein of each ChIFN was subcloned into its expression vector, expressed and purified and subsequently analysed using SDS-PAGE. The expected molecular weight of expressed ChIFNα and ChIFNλ was approximately 22 kDa (FIGS. 5A and C). The pET32a expression system used for ChIFNβ resulted in an expected molecular weight of approximately 34 kDa (FIG. 5B).

Figure 6:
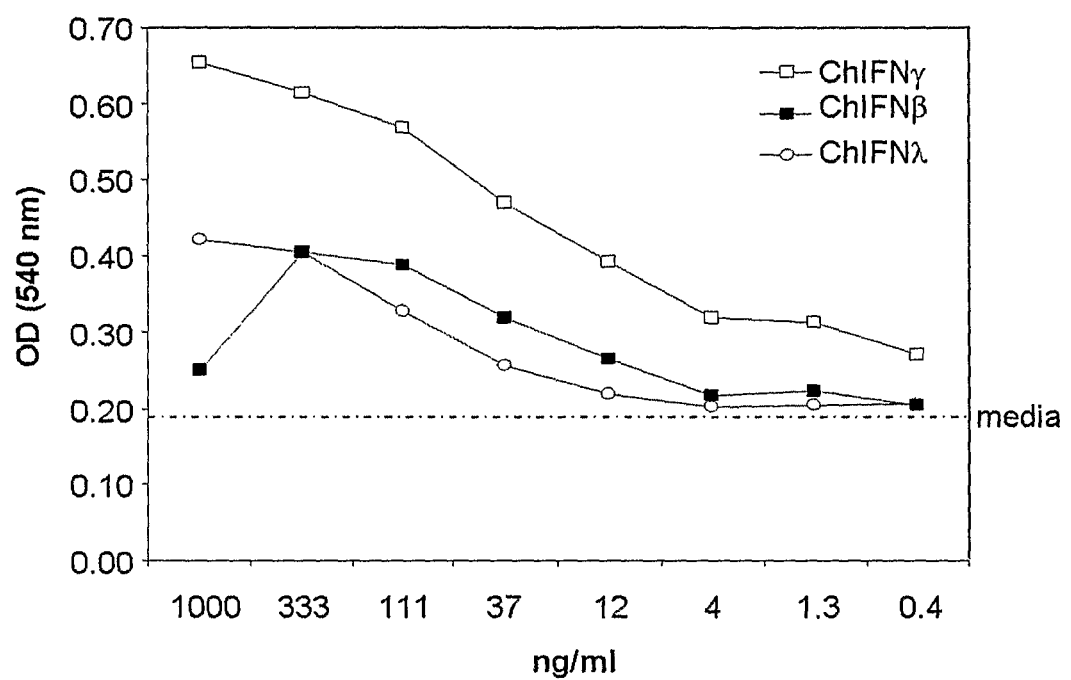
FIG. 6 is a graphical representation of nitrite production stimulated by chicken IFN. HD11 chicken macrophage-like cells were cultured with the ChIFNλ and ChIFNβ for 24 h and then supernatant tested for the presence of induced nitrite production. Displayed values are the mean of each experiment carried out in triplicate. Results are representative of 2 independent experiments.

ChIFNλ Stimulates Nitric Oxide Production Similar to ChIFNβ in HD11 Chicken Macrophage-like Cells The production of reactive oxygen and nitrogen species (ROS) is an important cellular inhibitory mechanism of virus (Schroder et al., 2004). ChIFNγ has been shown to stimulate the production of metabolites that impact nitric oxide levels (Lowenthal et al., 1995). To test the nitric oxide enhancing activity of ChIFNλ, HD11 cells were treated with 2-fold dilutions of recombinant (r) ChIFNλ and compared with rChIFNγ and rChIFNβ. RChIFNλ enhanced the production of nitric oxide similar to rChIFNβ (FIG. 6). RChIFNγ demonstrated the highest nitric oxide activity of the IFN tested (FIG. 6).

In vitro Bioactivity of ChIFNλ is Lower than ChIFNα

Figure 7:
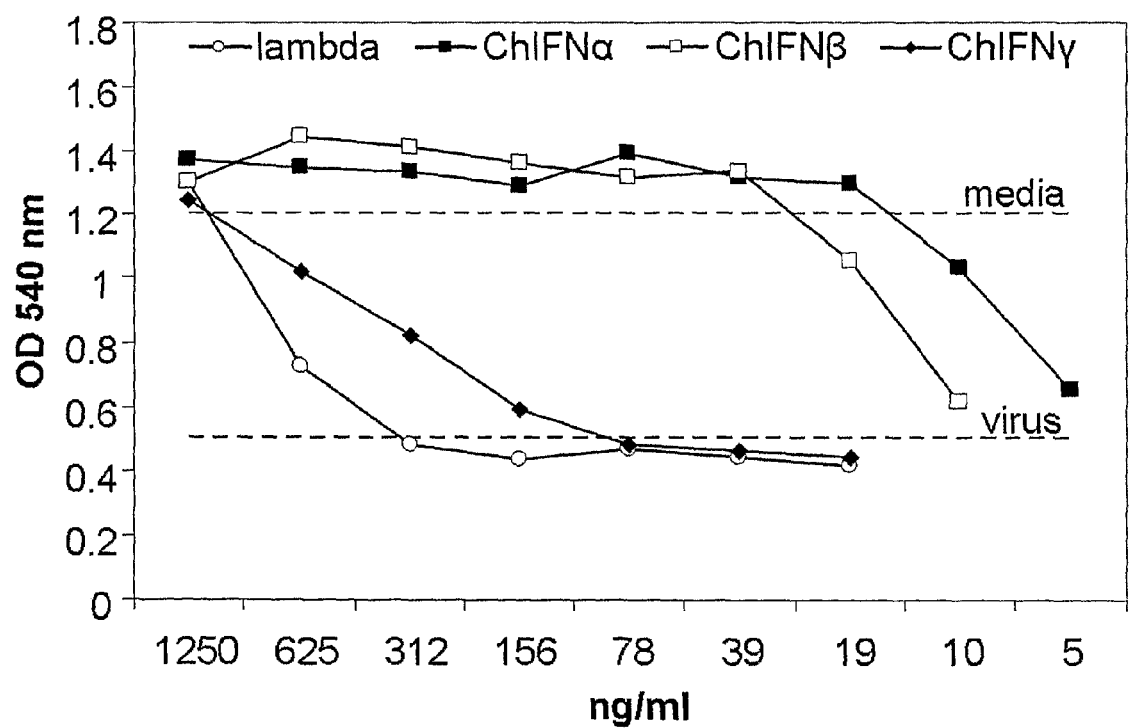
FIG. 7 is a graphical representation showing protection from SFV in CEF cells following treatment with IFN. CEF cells were cultured with various ChIFNs for 18 h then infected with SFV. Cytolysis was then measured by staining with neutral red and measuring absorbance ($OD_{540}$) at 24 h post-infection. Displayed values are the mean of experiment carried out in triplicate. Results are representative of 2 independent experiments.

To assess the viral inhibitory properties of ChIFNλ, the rChIFNα, and rChIFNλ and were compared in an SFV bioassay. Subsequent virus-induced cytolysis was reduced by each rChIFN in CEF cells (FIG. 7).

ChIFNλ has an Inhibitory Impact on Influenza Virus (PR8)

Figure 8:
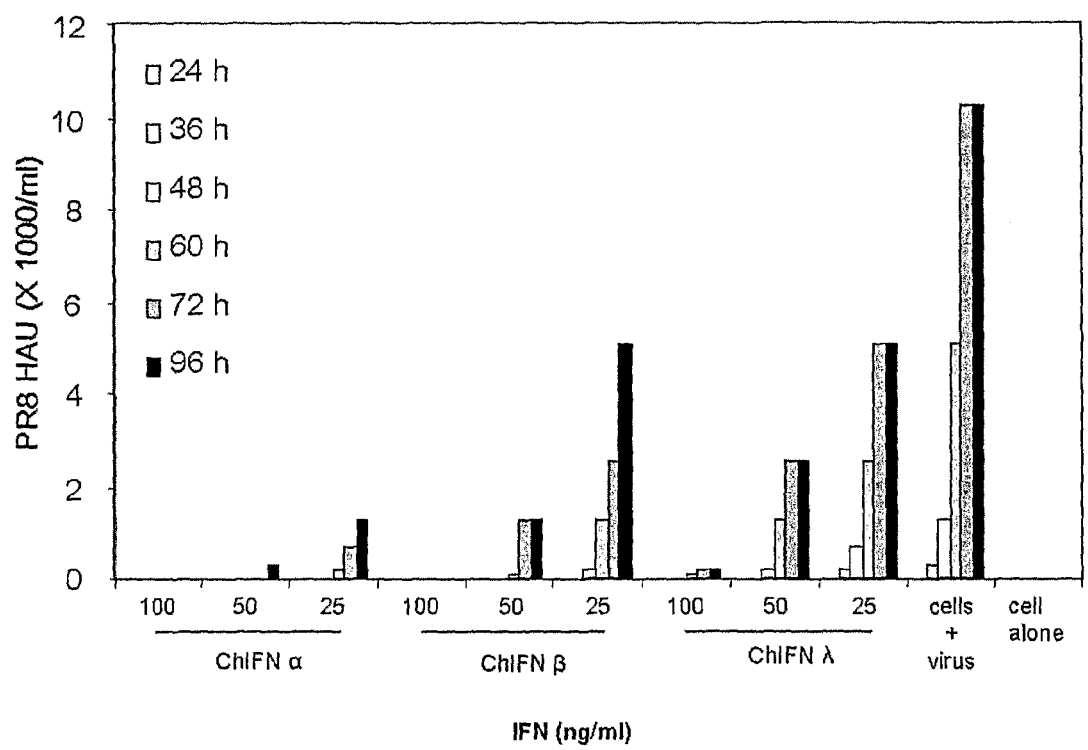
FIG. 8 is a graphical representation showing reduction of influenza in HD11 chicken macrophages following IFN pretreatment. HD11 cells were treated with ChIFNα, ChIFNβ, ChIFNλ or media alone for 6 h and then infected with influenza (PR8). The virus titre was measured at various timepoints post-infection by HA assay. Displayed values are the mean of each experiment carried out in quadruplicate. Results are representative of 2 independent experiments.

Since ChIFNλ displayed viral inhibition effects against SFV, the determination of inhibitory effects with regard to influenza virus was investigated. HD11 cells pretreated with rChIFNα, rChIFNβ or rChIFNλ and then infected with PR8, displayed various concentration-dependent levels of protection from PR8 as determined by HA assay (FIG. 8). At the high rChIFNλ dose (100 ng/ml) the virus titre was reduced compared to untreated cells across all time points ranging from no virus at 40 h post infection (pi) to 320 HAU at 90 h pi (FIG. 8). The lowest dose (25 ng/ml) resulted in some protection with an intermediate effect resulting from the intermediate dose (50 ng/ml) (FIG. 8). This clearly demonstrated that IFNλ inhibited influenza in chicken macrophages. The application of rChIFNα had the largest protective effect ranging in no detection of virus at the highest dose (100 ng/ml), to 1280 HAU/ml at the lowest dose (25 ng/ml) 90 h (pi) (FIG. 8). ChIFNβ also provided protection that ranged from no virus detection at the high dose (100 ng/ml) to 5120 HAU/ml at the lowest dose (25 ng/ml) 90 h pi (FIG. 8). Overall, all the IFN tested inhibited influenza titres in a dose-dependent manner.

Chicken Leukocytes Upregulate IFNλ Similarly to Type 1 IFN

Figure 9:
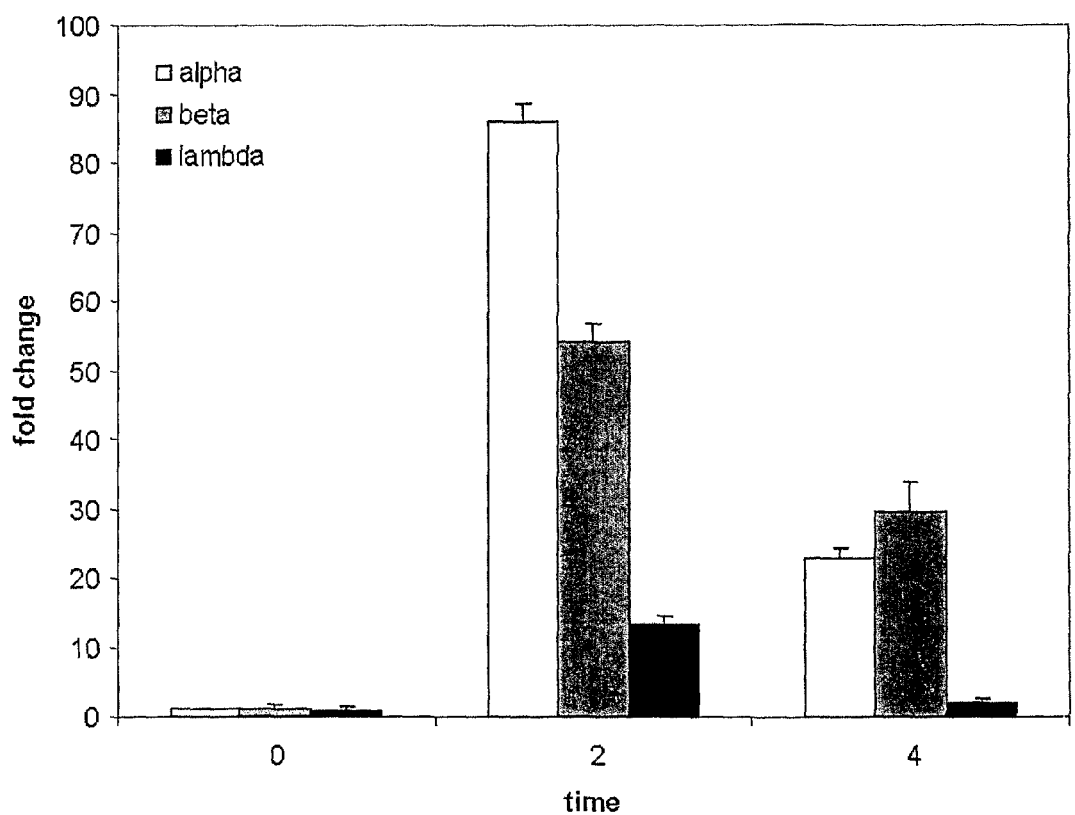
FIG. 9 is a graphical representation showing Poly (I:C) induction of IFN mRNA expression. Chicken splenic mononuclear cells were cultured with 30 μg/ml Poly (I:C) for 2 and 4 h. Subsequently, cells were harvested and ChIFNα, ChIFNβ and ChIFNλ mRNA levels were measured using qRT-PCR. The data represents the expression of the various IFN relative to unstimulated controls. GAPDH was used as a housekeeping gene to standardise results. The values are the mean and error bars represent SE. Experiments were carried out in triplicate and results are representative of 2 independent experiments.

Since IFNλ appeared to function similar to a type 1 IFN in the context of an antiviral response, whether ChIFNλ may be induced in a fashion similar to the type 1 IFN, ChIFNα and ChIFNβ was determined. Therefore Poly (I:C) was used to stimulate splenic leukocytes and the mRNA levels for ChIFNα, ChIFNβ, and ChIFNλ were measured by qRT-PCR. All 3 ChIFN were found to be upregulated 2 h post stimulation (FIG. 9). ChIFNα, mRNA increased 86-fold, ChIFNβ 52-fold and ChIFNλ 15-fold (FIG. 9). The extent of IFN upregulation was reduced for all IFN at 4 h post stimulation (FIG. 9). ChIFNλ was upregulated less than either ChIFNα or ChIFNβ.

TLR3 is Induced by Type 1 IFN but not by IFNλ

Figure 10:
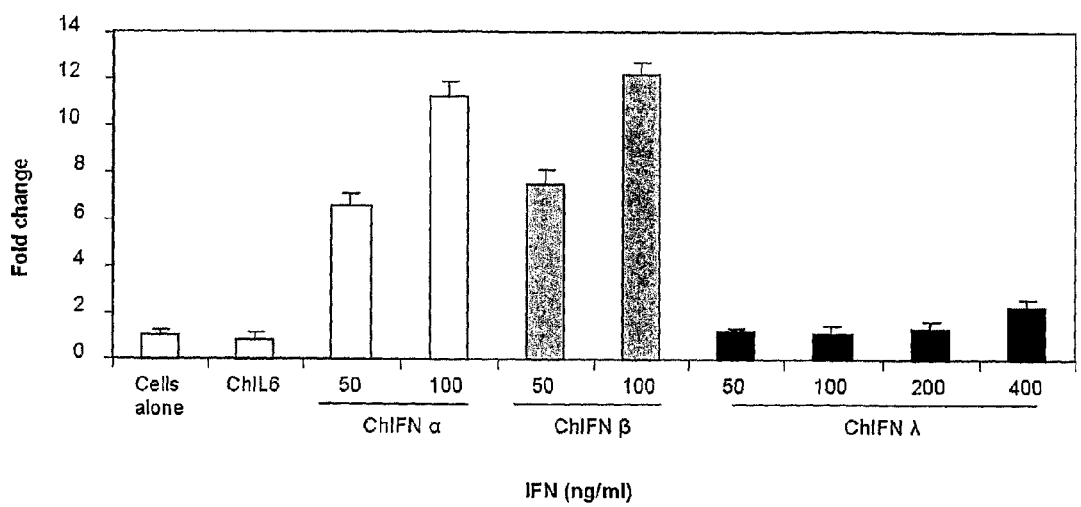
FIG. 10 is a graphical representation showing IFN induction of TLR3 mRNA expression. Chicken splenic mononuclear cells were cultured with ChIFNα, ChIFNβ and ChIFNλ at various concentrations for 3 h and then TLR3 mRNA levels measured using qRT-PCR. GAPDH was used as a housekeeping gene to standardise results. Expression is shown relative to unstimulated controls. The values are the mean and error bars represent SE. Experiments were carried out in triplicate and results are representative of 2 independent experiments.
Figure 11:
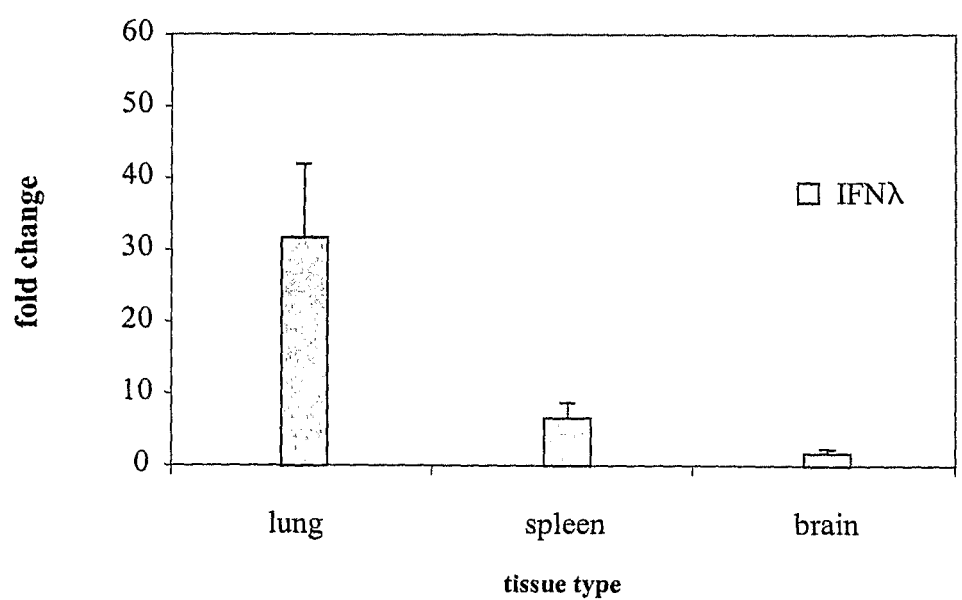
FIG. 11 is a graphical representation showing that IFNλ is induced during H5N1 (avian influenza) infection. The cytokine IFNλ was measured by qRT-PCR in chicken lung, spleen and brain following H5N1 (V/1203) infection. Data shows fold change compared to uninfected control birds. Data represents the mean (n=7), error bars show SE.
Figure 12:
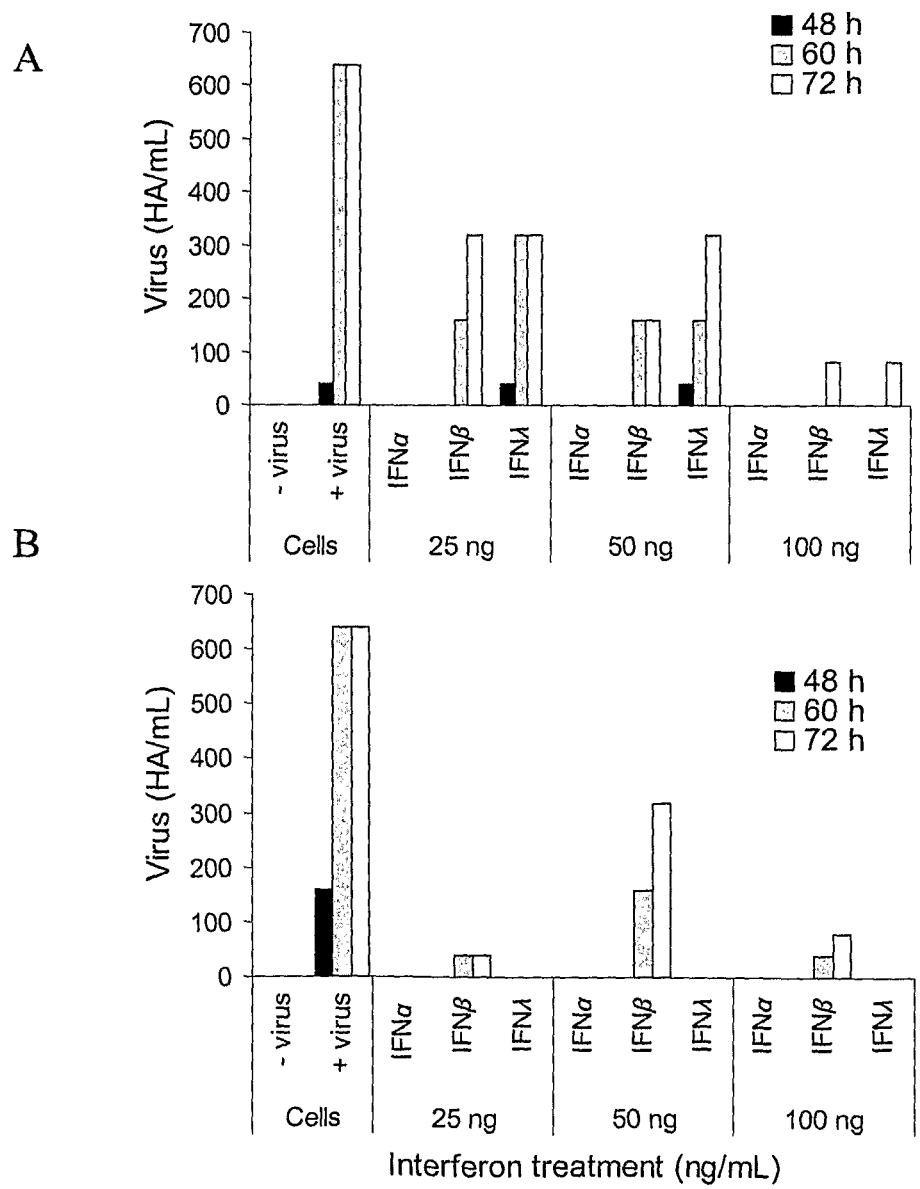
FIG. 12 is a graphical representation showing that IFNλ protects from influenza infection both pre- and post-infection. HD11 cells were either pretreated with chIFN-α, β and λ (B) or post-treated (A) at three concentrations then challenged with influenza (PR8). Bars show relative levels of virus as measured by HA at 24, 40, 48, 60 and 72 hours. No virus was detectable at 24 and 40 hours. Multiple samples were obtained at each timepoint.
Figure 13:
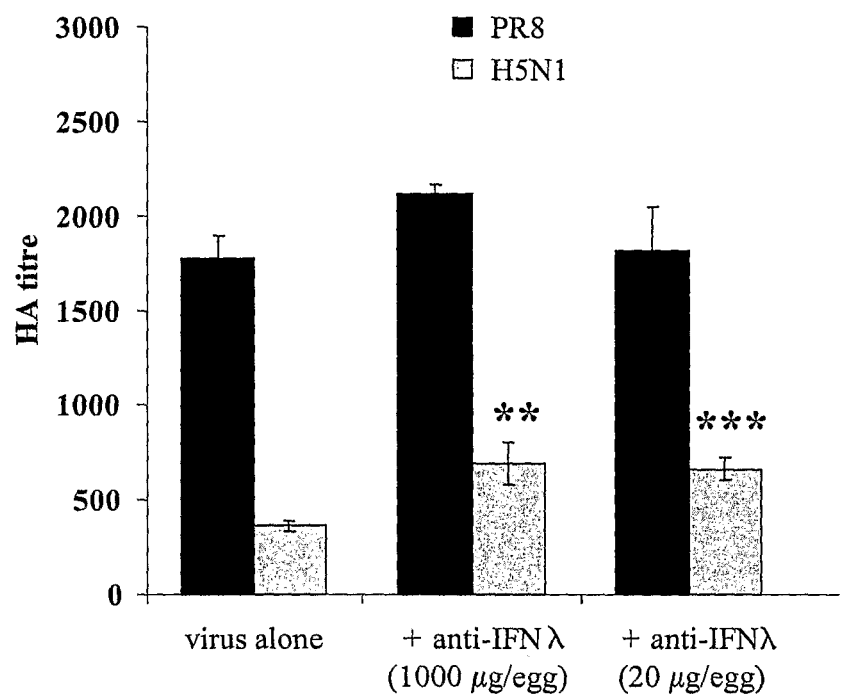
FIG. 13 is a graphical representation showing inhibition of IFNλ activity by antibodies against IFNλ. Anti-chIFN-λ antibodies co-inoculated with influenza vaccine virus in ovo increased influenza virus titres as determined by HA titre. Data represents the means of up to 7 experiments±SE. The statistical signific and diagnosis/monitoring of, inter alia, avian disease conditions associated with exposure to or infection with a pathogenic organism.
Figure 14:
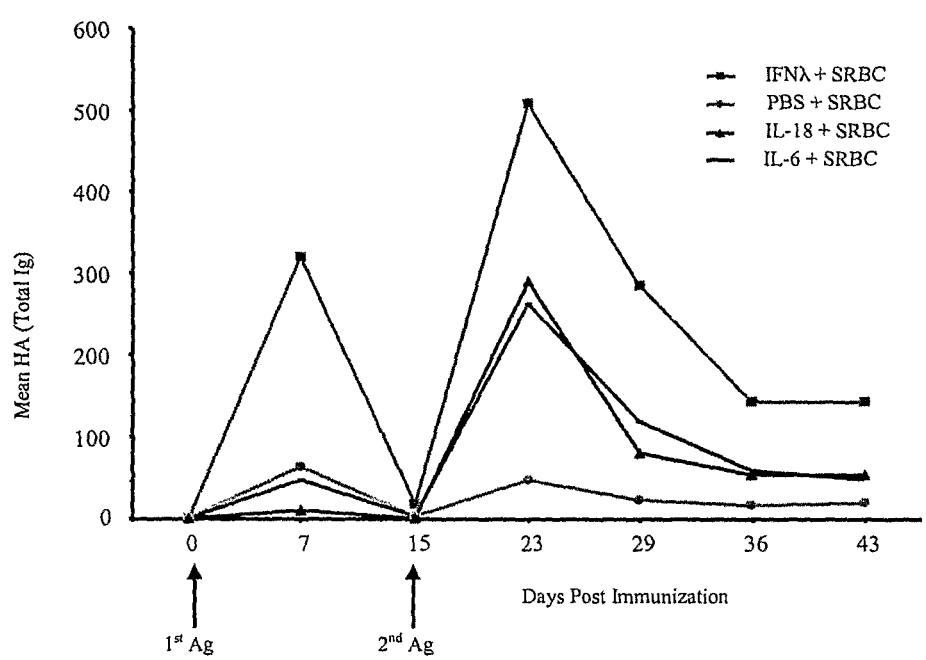
Figure 15:
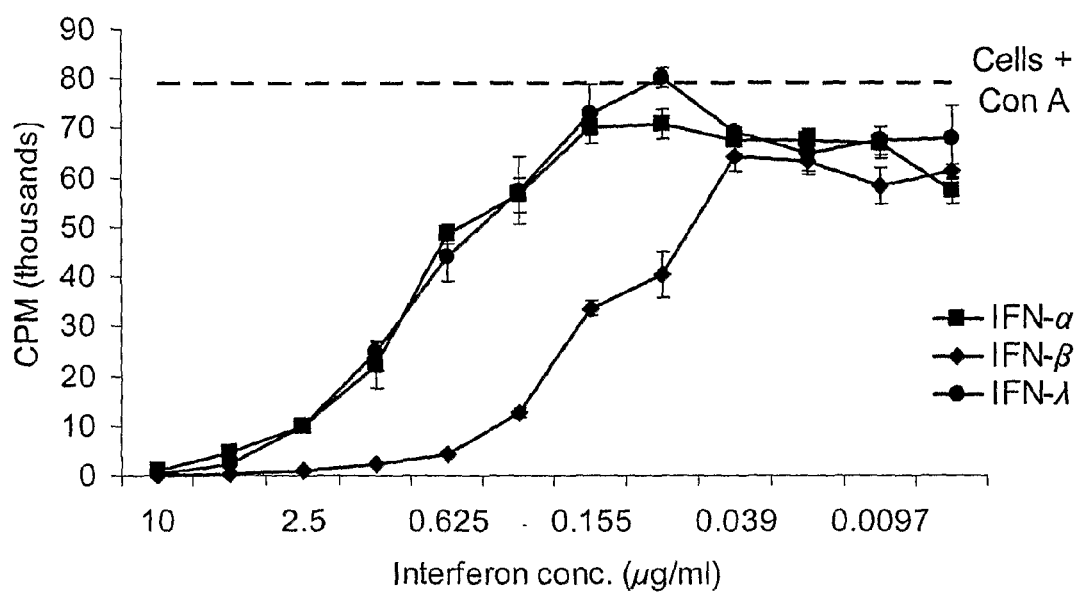

Whether type 1 IFN inducible genes could be induced similarly by ChIFNλ was investigated. Previous studies show that TLR3, an antiviral-related receptor, is a type 1 ISG (Tissari et al., 2005). Chicken splenic leukocytes were therefore cultured with rChIFNα, rChIFNβ or rChIFNλ, which revealed that only the type 1 IFN (rChIFNα, rChIFNβ) significantly induced TLR3 (FIG. 10). RChIFNα and rChIFNβ induced TLR3 6.6-fold and 7.5-fold respectively following application of 50 ng/ml for 2 h, and 11.3-fold and 12.3-fold at the higher dose of 100 ng/ml (FIG. 10) whereas rChIFNλ had little effect on TLR3 induction.

EXAMPLE 2

Methods

H5N1 virus A/Vietnam/1203/04 (V/1203) influenza virus was passaged in the allantoic fluid of 10-day embryonated Specific Pathogen Free (SPF) chicken eggs. The allantoic fluid was harvested and aliquoted then stored at −80° C. for inoculations. SPF white leghorn chickens (4 weeks old) were inoculated intraocularly with 50 egg infectious doses ($EID_{50}$) of V/1203. At 24 h post infection (p.i.) chickens were euthanised and samples of tissue were immediately harvested for RNA extraction and subsequent qRT-PCR analyses of IFNλ.

Virus protection using IFNλ was carried out according to the method described in Karpala, A. J., K. R. Morris, M. M. Broadway, P. G. McWaters, T. E. O'Neil, K. E. Goossens, J. W. Lowenthal, and A. G. Bean. 2008. Molecular cloning, expression, and characterization of chicken IFN-lambda. J Interferon Cytokine Res 28:341-50.

In ovo inoculation of influenza virus and antisera was carried out by diluting purified anti-chIFNλ at either 1000 μg, or 20 μg per egg. Two hundred μL of anti-chIFN-antibody was injected into the allantoic fluid of each egg with 200 μL of the vaccine virus. After 48 h 5 mL of allantoic fluid was removed from each egg and virus titres were determined by haemagglutinin assay (Karpala et al., 2008).

IFNλ adjuvant activity was assayed by injecting sheep red blood cells (SRBC) with or without IFNλ. Four groups of SPF chickens were injected with 0.01 ml SRBC the respective adjuvant at d 0 and then further injected with SRBC alone again at d 15.

Chickens were bled at various timepoints and total antibodies determined by HA according to the method of Van der Zijpp and Leenstra, Poultry Sci. 59:1363-1369.

Results

IFNλ expression is induced following H5N1 (avian influenza) infection in the chicken (FIG. 11). It was demonstrated that the application of IFNλ protected against influenza in vitro both pre- and post-infection, however, protection was further enhanced when IFNλ was applied prior to infection (FIG. 12). These findings were consistent with the fact that the inhibition of chIFNλ activity (by an antibody against IFNλ) augmented the growth of influenza vaccine in eggs (FIG. 13).

IFNλ was demonstrated to exhibit adjuvant potential since it stimulated the production of antibodies following inoculation of an antigen (sheep red blood cells) (FIG. 14). The application of IFNλ inhibited ConA induced lymphocyte proliferation (FIG. 15).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Abend J. R., Low J. A. and Imperiale M. J. (2007) Inhibitory effect of gamma interferon on BK virus gene expression and replication. *J Virol* 81, 272-9.

Ank N., West H., Bartholdy C., Eriksson K., Thomsen A. R. and Paludan S. R. (2006) Lambda interferon (IFN-lambda), a type III IFN, is induced by viruses and IFNs and displays potent antiviral activity against select virus infections in vivo. *J Virol* 80, 4501-9.

Annibali V., Giovanni S. D., Cannoni S., Giugni E., Bomprezzi R., Mattei C., Elkahloun A., Coccia E. M., Alfo M., Orzi F., Ristori G. and Salvetti M. (2007) Gene expression profiles reveal homeostatic dynamics during interferon-beta therapy in multiple sclerosis. *Autoimmunity* 40, 16-22.

Beilharz M. W., Cummins J. M. and Bennett A. L. (2007) Protection from lethal influenza virus challenge by oral type 1 interferon. *Biochem Biophys Res Commun* 355, 740-4.

Bracci L., Canini I., Puzelli S., Sestili P., Venditti M., Spada M., Donatelli I., Belardelli F. and Proietti E. (2005) Type I IFN is a powerful mucosal adjuvant for a selective intranasal vaccination against influenza virus in mice and affects antigen capture at mucosal level. *Vaccine* 23, 2994-3004.

Chen J. M., Chen J. W., Dai J. J. and Sun Y. X. (2007) A survey of human cases of H5N1 avian influenza reported by the WHO before June 2006 for infection control. *Am J Infect Control* 35, 351-3.

Chesler D. A., Munoz-Jordan J. L., Donelan N., Garcia-Sastre A. and Reiss C. S. (2003) PKR is not required for interferon-gamma inhibition of VSV replication in neurons. *Viral Immunol* 16, 87-96.

de Veer M. J., Holko M., Frevel M., Walker E., Der S., Paranjape J. M., Silverman R. H. and Williams B. R. (2001) Functional classification of interferon-stimulated genes identified using microarrays. *J Leukoc Biol* 69, 912-20.

Digby M. R. and Lowenthal J. W. (1995) Cloning and expression of the chicken interferon-gamma gene. *J Interferon Cytokine Res* 15, 939-45.

Donnelly R. P., Sheikh F., Kotenko S. V. and Dickensheets H. (2004) The expanded family of class II cytokines that share the IL-10 receptor-2 (IL-10R2) chain. *J Leukoc Biol* 76, 314-21.

Dumoutier L., Tounsi A., Michiels T., Sommereyns C., Kotenko S. V. and Renauld J. C. (2004) Role of the interleukin (IL)-28 receptor tyrosine residues for antiviral and antiproliferative activity of IL-29/interferon-lambda 1: similarities with type I interferon signaling. *J Biol Chem* 279, 32269-74.

Green L. C., Wagner D. A., Glogowski J., Skipper P. L., Wishnok J. S. and Tannenbaum S. R. (1982) Analysis of nitrate, nitrite, and. *Anal Biochem* 126, 131-8.

Jacobs B. L. and Langland J. O. (1996) When two strands are better than one: the mediators and modulators of the cellular responses to double-stranded RNA. *Virology* 219, 339-49.

Kaiser P., Poh T. Y., Rothwell L., Avery S., Balu S., Pathania U. S., Hughes S., Goodchild M., Morrell S., Watson M., Bumstead N., Kaufman J. and Young J. R. (2005) A genomic analysis of chicken cytokines and chemokines. *J Interferon Cytokine Res* 25, 467-84.

Kamijo R., Shapiro D., Gerecitano J., Le J., Bosland M. and Vilcek J. (1994) Biological functions of IFN-gamma and IFN-alpha/beta: lessons from studies in gene knockout mice. *Hokkaido Igaku Zasshi* 69, 1332-8.

Karpala, A. J., K. R. Morris, M. M. Broadway, P. G. McWaters, T. E. O'Neil, K. E. Goossens, J. W. Lowenthal, and A. G. Bean. 2008. Molecular cloning, expression, and characterization of chicken IFN-lambda. *J Interferon Cytokine Res* 28:341-50.

Koerner I., Kochs G., Kalinke U., Weiss S. and Staeheli P. (2007) Protective role of beta interferon in host defense against influenza A virus. *J Virol* 81, 2025-30.

Kotenko S. V., Gallagher G., Baurin V. V., Lewis-Antes A., Shen M., Shah N. K., Langer J. A., Sheikh F., Dickensheets H. and Donnelly R. P. (2003) MN-lambdas mediate antiviral protection through a distinct class II cytokine receptor complex. *Nat Immunol* 4, 69-77.

Li Y. C., Kong L. H., Cheng B. Z. and Li K. S. (2005) Construction of influenza virus siRNA expression vectors and their inhibitory effects on multiplication of influenza virus. *Avian Dis* 49, 562-73.

Lowenthal J. W., Digby M. R. and York J. J. (1995) Production of interferon-gamma by chicken T cells. *J Interferon Cytokine Res* 15, 933-8.

Majde J. A. (2000) Viral double-stranded RNA, cytokines, and the flu. *J Interferon Cytokine Res* 20, 259-72.

Marcello T., Grakoui A., Barba-Spaeth G., Machlin E. S., Kotenko S. V., MacDonald M. R. and Rice C. M. (2006) Interferons alpha and lambda inhibit hepatitis C virus replication with distinct signal transduction and gene regulation kinetics. *Gastroenterology* 131, 1887-98.

Meager A., Visvalingam K., Dilger P., Bryan D. and Wadhwa M. (2005) Biological activity of interleukins-28 and -29: comparison with type I interferons. *Cytokine* 31, 109-18.

Meager A. (2002) Biological assays for interferons. *J Immunol Methods* 261, 21-36.

Migliorini P., Corradin G. and Corradin S. B. (1991) Macrophage NO2-production as a sensitive and rapid assay for the quantitation of murine IFN-gamma. *J Immunol Methods* 139, 107-14.

Moraes M. P., de Los Santos T., Koster M., Turecek T., Wang H., Andreyev V. G. and Grubman M. J. (2007) Enhanced antiviral activity against foot-and-mouth disease virus by a combination of type I and II porcine interferons. *J Virol* 81, 7124-35.

Rio J., Nos C., Marzo M. E., Tintore M. and Montalban X. (1998) Low-dose steroids reduce flu-like symptoms at the initiation of IFNbeta-1b in relapsing-remitting MS. *Neurology* 50, 1910-2.

Robek M. D., Boyd B. S. and Chisari F. V. (2005) Lambda interferon inhibits hepatitis B and C virus replication. *J Virol* 79, 3851-4.

Schroder K., Hertzog P. J., Ravasi T. and Hume D. A. (2004) Interferon-gamma: an overview of signals, mechanisms and functions. *J Leukoc Biol* 75, 163-89.

Schultz U., Kaspers B. and Staeheli P. (2004) The interferon system of non-mammalian vertebrates. *Dev Comp Immunol* 28, 499-508.

Sekellick M. J., Ferrandino A. F., Hopkins D. A. and Marcus P. I. (1994) Chicken interferon gene: cloning, expression, and analysis. *J Interferon Res* 14, 71-9.

Sheppard P., Kindsvogel W., Xu W., Henderson K., Schlutsmeyer S., Whitmore T. E., Kuestner R., Garrigues U., Birks C., Roraback J., Ostrander C., Dong D., Shin J., Presnell S., Fox B., Haldeman B., Cooper E., Taft D., Gilbert T., Grant F. J., Tackett M., Krivan W., McKnight G., Clegg C., Foster D. and Klucher K. M. (2003) IL-28, IL-29 and their class II cytokine receptor IL-28R. *Nat Immunol* 4, 63-8.

Smith C. A., McClive P. J., Western P. S., Reed K. J. and Sinclair A. H. (1999) Conservation of a sex-determining gene. *Nature* 402, 601-2.

Smith P. L., Lombardi G. and Foster G. R. (2005) Type I interferons and the innate immune response—more than just antiviral cytokines. *Mol Immunol* 42, 869-77.

Stohr K. and Esveld M. (2004) Public health. Will vaccines be available for the next influenza pandemic? *Science* 306, 2195-6.

Sung Y. J., Hotchkiss J. H., Austic R. E. and Dieted R. R. (1991) L-arginine-dependent production of a reactive nitrogen intermediate by macrophages of a uricotelic species. *J Leukoc Biol* 50, 49-56.

Takaoka A. and Yanai H. (2006) Interferon signalling network in innate defense. *Cell Microbiol* 8, 907-22.

Tanabe M., Kurita-Taniguchi M., Takeuchi K., Takeda M., Ayata M., Ogura H., Matsumoto M. and Seya T. (2003) Mechanism of up-regulation of human Toll-like receptor 3 secondary to infection of measles virus-attenuated strains. *Biochem Biophys Res Commun* 311, 39-48.

Theofilopoulos A. N., Baccala R., Beutler B. and Kono D. H. (2005) Type I interferons (alpha/beta) in immunity and autoimmunity. *Annu Rev Immunol* 23, 307-36.

Tissari J., Siren J., Meri S., Julkunen I. and Matikainen S. (2005) IFN-alpha enhances TLR3-mediated antiviral cytokine expression in human endothelial and epithelial cells by up-regulating TLR3 expression. *J Immunol* 174, 4289-94.

Zoller B., Redman-Muller I., Nanda I., Guttenbach M., Dosch E., Schmid M., Zoorob R. and Jungwirth C. (2000) Sequence comparison of avian interferon regulatory factors and identification of the avian CEC-32 cell as a quail cell line. *J Interferon Cytokine Res* 20, 711-7.

TABLE 3

Primer sequences used in this study

| Chicken IFN | Primer name | Type | Sequence 5'-3' |
|---|---|---|---|
| α | α1 | F seq | atggctgtgcctgcaagcc (SEQ ID NO: 5) |
|  | α2 | R seq | ctaagtgcgcgtgttgcctgtg (SEQ ID NO: 6) |
|  | α3 | F exp | actggatcctgcaaccacttcgcccc (SEQ ID NO: 7) |
|  | α4 | R exp | actaagcttctaagtgcgcgtgttgcctg (SEQ ID NO: 8) |
| β | β1 | F seq | atgactgcaaaccatcag (SEQ ID NO: 9) |
|  | β2 | R seq | tcactgggtgttgagacg (SEQ ID NO: 10) |
|  | β3 | F exp | actggatccttctectgcaaccatcttc (SEQ ID NO: 11) |
|  | β4 | R exp | actaagctttcactgggtgttgagacg (SEQ ID NO: 12) |
| λ | λ1 | F seq | atggtatgctacggggtcac (SEQ ID NO: 13) |
|  | λ2 | R seq | ctaagtgcaatcctcgcgctg (SEQ ID NO: 14) |
|  | λ3 | F exp | actggatccttcccccaggtcaccccgaag (SEQ ID NO: 15) |
|  | λ4 | R exp | actaagcttctaagtgcaatcctcgcgctg (SEQ ID NO: 16) |

TABLE 4

Similarity of ChIFNλ to IFNλ of other species and other chicken cytokines

| Cytokine group | Cytokine | % identical ORF (nucleotides) | No. of aa residues | % identical aa | Genbank accession no. |
|---|---|---|---|---|---|
| IFN λ | hIFNλ1 | 51 | 200 | 30 | NM 172140 |
|  | hIFNλ2 | 53 | 200 | 36 | NM 172138 |
|  | hIFNλ3 | 52 | 196 | 34 | NM 172139 |
|  | mIFNλ2 | 49 | 193 | 31 | AY869695 |
|  | zIFNλ | 45 | 196 | 20 | AB093588 |
| ChIFN | ChIFNα | 43 | 193 | 19 | X92477 |
|  | ChIFNβ | 46 | 203 | 16 | AY831397 |
|  | ChIFNγ | 42 | 164 | 17 | NM 205149 |
|  | chIL10 | 48 | 175 | 17 | NM 001004414 |
|  | chIL20 | 43 | 176 | 14 | XM 425824 |
| Other ch IL | chIL5 | 41 | 136 | 14 | NM 001007084 |
|  | chIL13 | 44 | 138 | 18 | NM 001007085 |
|  | ChIL1β | 38 | 267 | 16 | NM 204524 |

The invention claimed is:

1. A method for the treatment of a pathogen infection in an aves comprising administering to said aves an effective amount of:
   (i) an isolated polypeptide wherein said polypeptide comprises the amino acid sequence as set forth in SEQ ID NO:2 or 4; or
   (ii) a fusion polypeptide between the polypeptide of (i) and either:
      a) a Type III interferon, or
      b) a Type I or Type II interferon such as one which is selected from the group consisting of IFN-α, IFN-β, IFN-γ, Ch IFN-α, Ch IFN-β, and Ch IFN-γ.

2. The method according to claim 1, wherein said pathogen is a virus, bacterium, or parasite.

3. The method of claim 1, wherein said aves is a chicken, turkey, bantam, quail, guinea fowl, duck, goose, ostrich, emu, pigeon, canary, budgerigar, parrot or finch.

4. The method according to claim 1, wherein said polypeptide is administered in combination with a second avian cytokine molecule selected from the group consisting of a Type III interferon, a Type I interferon, Type II interferon, IFN-α, IFN-β, IFN-γ, Ch IFN-α, Ch IFN-β, and Ch IFN-γ.

5. The method according to claim 1, wherein said polypeptide is formulated for administration to the avian animal by ingestion, injection in ovo, post-hatching injection, intraperitoneal injection, intra-dermal injection, intra-muscular injection, intra-ocular injection, intravenous injection or subcutaneous injection.

6. A method for inducing or upregulating an immune response in an aves said method comprising administering to said aves an effective amount of:
   (i) an isolated polypeptide wherein said polypeptide comprises the amino acid sequence as set forth in SEQ ID NO:2 or 4; or
   (ii) a fusion polypeptide between the polypeptide of (i) and either:
      a) a Type III interferon, or
      b) a Type I or Type II interferon such as one which is selected from the group consisting of IFN-α, IFN-β, IFN-γ, Ch IFN-α, Ch IFN-β, and Ch IFN-γ.

* * * * *

SEQUENCE LISTING

```
<160> NUMBER OF SEQ ID NOS: 20

<210> SEQ ID NO 1
<211> LENGTH: 561
<212> TYPE: DNA
<213> ORGANISM: Gallus gallus

<400> SEQUENCE: 1
atggtatgct acggggtcac aattattttg gtggggaccc tggggtccct cctggtgggt      60
gccttccccc aggtcacccc gaagaagagc tgcagcctct ccaagtacca gttccctgca     120
cctttggagt tgaaggcagt gtggaggatg aaggagcagt tgaagacat catgctgtta      180 acaaacagaa aatgcaacac cagactcttc catcggaagt gggacatagc tgagctgtcg     240
gtacctgacc gaatcaccct ggtggaggct gagctggacc tcaccatcac cgtgctcaca     300 aacccacaa cccagagact ggcagagacg tgccaacagc cctggcctt ccttacccaa       360 gtccaggagg acctgcgaga ctgcttggcc ctcgaggcac cttcacatca gccctctggg     420
aaactgaggc actggctgca gaagctgaag acagccaaga gaaggagac cgccggctgc     480 ctggaggcct cagccatcct ccacatcttc caagtactga acgacctgcg gtgcgcagcc     540
cagcgcgagg attgcactta g                                               561

<210> SEQ ID NO 2
<211> LENGTH: 186
<212> TYPE: PRT
<213> ORGANISM: Gallus gallus

<400> SEQUENCE: 2

Met Val Cys Tyr Gly Val Thr Ile Ile Leu Val Gly Thr Leu Gly Ser
1               5                   10                  15

Leu Leu Val Gly Ala Phe Pro Gln Val Thr Pro Lys Lys Ser Cys Ser
            20                  25                  30

Leu Ser Lys Tyr Gln Phe Pro Ala Pro Leu Glu Leu Lys Ala Val Trp
        35                  40                  45

Arg Met Lys Glu Gln Phe Glu Asp Ile Met Leu Leu Thr Asn Arg Lys
    50                  55                  60

Cys Asn Thr Arg Leu Phe His Arg Lys Trp Asp Ile Ala Glu Leu Ser
65                  70                  75                  80

Val Pro Asp Arg Ile Thr Leu Val Glu Ala Glu Leu Asp Leu Thr Ile
                85                  90                  95

Thr Val Leu Thr Asn Pro Thr Thr Gln Arg Leu Ala Glu Thr Cys Gln
```

```
            100                 105                 110
Gln Pro Leu Ala Phe Leu Thr Gln Val Gln Glu Asp Leu Arg Asp Cys
        115                 120                 125

Leu Ala Leu Glu Ala Pro Ser His Gln Pro Ser Gly Lys Leu Arg His
        130                 135                 140

Trp Leu Gln Lys Leu Lys Thr Ala Lys Lys Glu Thr Ala Gly Cys
145                 150                 155                 160

Leu Glu Ala Ser Ala Ile Leu His Ile Phe Gln Val Leu Asn Asp Leu
                165                 170                 175

Arg Cys Ala Ala Gln Arg Glu Asp Cys Thr
                180                 185

<210> SEQ ID NO 3
<211> LENGTH: 498
<212> TYPE: DNA
<213> ORGANISM: Gallus gallus

<400> SEQUENCE: 3
ttcccccagg tcaccccgaa gaagagctgc agcctctcca gtaccagttt ccctgcacct      60
ttggagttga aggcagtgtg gaggatgaag gagcagtttg aagacatcat gctgttaaca     120
aacagaaaat gcaacaccag actcttccat cggaagtggg acatagctga gctgtcggta     180
cctgaccgaa tcaccctggt ggaggctgag ctggacctca ccatcaccgt gctcacaaac     240
cccacaaccc agagactggc agagacgtgc aacagcccc tggccttcct tacccaagtc      300
caggaggacc tgcgagactg cttggccctc gaggcacctt cacatcagcc ctctgggaaa     360
ctgaggcact ggctgcagaa gctgaagaca gccaagaaga aggagaccgc cggctgcctg     420
gaggcctcag ccatcctcca catcttccaa gtactgaacg acctgcggtg cgcagcccag     480
cgcgaggatt gcacttag                                                  498

<210> SEQ ID NO 4
<211> LENGTH: 165
<212> TYPE: PRT
<213> ORGANISM: Gallus gallus

<400> SEQUENCE: 4

Phe Pro Gln Val Thr Pro Lys Lys Ser Cys Ser Leu Ser Lys Tyr Gln
1               5                  10                  15

Phe Pro Ala Pro Leu Glu Leu Lys Ala Val Trp Arg Met Lys Glu Gln
                20                  25                  30

Phe Glu Asp Ile Met Leu Leu Thr Asn Arg Lys Cys Asn Thr Arg Leu
            35                  40                  45

Phe His Arg Lys Trp Asp Ile Ala Glu Leu Ser Val Pro Asp Arg Ile
        50                  55                  60

Thr Leu Val Glu Ala Glu Leu Asp Leu Thr Ile Thr Val Leu Thr Asn
65                  70                  75                  80

Pro Thr Thr Gln Arg Leu Ala Glu Thr Cys Gln Pro Leu Ala Phe
                85                  90                  95

Leu Thr Gln Val Gln Glu Asp Leu Arg Asp Cys Leu Ala Leu Glu Ala
            100                 105                 110

Pro Ser His Gln Pro Ser Gly Lys Leu Arg His Trp Leu Gln Lys Leu
        115                 120                 125

Lys Thr Ala Lys Lys Glu Thr Ala Gly Cys Leu Glu Ala Ser Ala
        130                 135                 140

Ile Leu His Ile Phe Gln Val Leu Asn Asp Leu Arg Cys Ala Ala Gln
```

```
                145                 150                 155                 160
Arg Glu Asp Cys Thr
            165

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
atggctgtgc ctgcaagcc                                                   19

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
ctaagtgcgc gtgttgcctg tg                                               22

<210> SEQ ID NO 7
<211> LENGTH: 27
<212> TYPE: DNA
<213> ORGANISM: Artificial Sequence
<220> FEATURE:
<223> OTHER INFORMATION: Primer

<400> SEQUENCE: 7
actggatcct gcaaccacct tcgcccc                                          27

<210> SEQ ID NO 8
<211> LENGTH: 29
<212> TYPE: DNA
<213> ORGANISM: Artificial Sequence
<220> FEATURE:
<223> OTHER INFORMATION: Primer

<400> SEQUENCE: 8
actaagcttc taagtgcgcg tgttgcctg                                        29

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
atgactgcaa accatcag                                                    18

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
tcactgggtg ttgagacg                                                    18

<210> SEQ ID NO 11
```

```
<210> SEQ ID NO 11
<211> LENGTH: 28
<212> TYPE: DNA
<213> ORGANISM: Artificial Sequence
<220> FEATURE:
<223> OTHER INFORMATION: Primer

<400> SEQUENCE: 11
actggatcct tctcctgcaa ccatcttc                                          28

<210> SEQ ID NO 12
<211> LENGTH: 27
<212> TYPE: DNA
<213> ORGANISM: Artificial Sequence
<220> FEATURE:
<223> OTHER INFORMATION: Primer

<400> SEQUENCE: 12
actaagcttt cactgggtgt tgagacg                                           27

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
atggtatgct acggggtcac                                                   20

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
ctaagtgcaa tcctcgcgct g                                                 21

<210> SEQ ID NO 15
<211> LENGTH: 30
<212> TYPE: DNA
<213> ORGANISM: Artificial Sequence
<220> FEATURE:
<223> OTHER INFORMATION: Primer

<400> SEQUENCE: 15
actggatcct tcccccaggt caccccgaag                                        30

<210> SEQ ID NO 16
<211> LENGTH: 30
<212> TYPE: DNA
<213> ORGANISM: Artificial Sequence
<220> FEATURE:
<223> OTHER INFORMATION: Primer

<400> SEQUENCE: 16
actaagcttc taagtgcaat cctcgcgctg                                        30

<210> SEQ ID NO 17
<211> LENGTH: 200
<212> TYPE: PRT
<213> ORGANISM: Homo sapiens

<400> SEQUENCE: 17

Met Lys Leu Asp Met Thr Gly Asp Cys Thr Pro Val Leu Val Leu Met
```

```
                1               5                  10                 15
        Ala Ala Val Leu Thr Val Thr Gly Ala Val Pro Val Ala Arg Leu His
                        20                 25                 30

Gly Ala Leu Pro Asp Ala Arg Gly Cys His Ile Ala Gln Phe Lys Ser
                        35                 40                 45

Leu Ser Pro Gln Glu Leu Gln Ala Phe Lys Arg Ala Lys Asp Ala Leu
                50                         55                 60

Glu Glu Ser Leu Leu Lys Asp Cys Arg Cys His Ser Arg Leu Phe
        65                      70                 75                     80

Pro Arg Thr Trp Asp Leu Arg Gln Leu Gln Val Arg Glu Arg Pro Met
                                85                 90                 95

Ala Leu Glu Ala Glu Leu Ala Leu Thr Leu Lys Val Leu Glu Ala Thr
                        100                105                110

Ala Asp Thr Asp Pro Ala Leu Val Asp Val Leu Asp Gln Pro Leu His
                        115                120                125

Thr Leu His His Ile Leu Ser Gln Phe Arg Ala Cys Ile Gln Pro Gln
                        130                135                140

Pro Thr Ala Gly Pro Arg Thr Arg Gly Arg Leu His His Trp Leu Tyr
        145                     150                155                    160

Arg Leu Gln Glu Ala Pro Lys Lys Glu Ser Pro Gly Cys Leu Glu Ala
                        165                170                175

Ser Val Thr Phe Asn Leu Phe Arg Leu Leu Thr Arg Asp Leu Asn Cys
                        180                185                190

Val Ala Ser Gly Asp Leu Cys Val
                        195                200

<210> SEQ ID NO 18
<211> LENGTH: 193
<212> TYPE: PRT
<213> ORGANISM: M. musculus

<400> SEQUENCE: 18

Met Leu Leu Leu Leu Pro Leu Leu Leu Ala Ala Val Leu Thr Arg
        1               5                  10                 15

Thr Gln Ala Asp Pro Val Pro Arg Ala Thr Arg Leu Pro Val Glu Ala
                        20                 25                 30

Lys Asp Cys His Ile Ala Gln Phe Lys Ser Leu Ser Pro Lys Glu Leu
                        35                 40                 45

Gln Ala Phe Lys Lys Ala Lys Gly Ala Ile Glu Lys Arg Leu Leu Glu
                50                         55                 60

Lys Asp Met Arg Cys Ser Ser His Leu Ile Ser Arg Ala Trp Asp Leu
        65                      70                 75                     80

Lys Gln Leu Gln Val Gln Glu Arg Pro Lys Ala Leu Gln Ala Glu Val
                        85                 90                 95

Ala Leu Thr Leu Lys Val Trp Glu Asn Ile Asn Asp Ser Ala Leu Thr
                        100                105                110

Thr Ile Leu Gly Gln Pro Leu His Thr Leu Ser His Ile His Ser Gln
                        115                120                125

Leu Gln Thr Cys Thr Gln Leu Gln Ala Thr Ala Glu Pro Lys Pro Pro
                        130                135                140

Ser Arg Arg Leu Ser Arg Trp Leu His Arg Leu Gln Glu Ala Gln Ser
        145                     150                155                    160

Lys Glu Thr Pro Gly Cys Leu Glu Asp Ser Val Thr Ser Asn Leu Phe
                        165                170                175
```

```
Gln Leu Leu Arg Asp Leu Lys Cys Val Ala Ser Gly Asp Gln Cys
        180                 185                 190
Val

<210> SEQ ID NO 19
<211> LENGTH: 186
<212> TYPE: PRT
<213> ORGANISM: G. gallus

<400> SEQUENCE: 19

Met Val Cys Tyr Gly Val Thr Ile Ile Leu Val Gly Thr Leu Gly Ser
1               5                   10                  15

Leu Leu Val Gly Ala Phe Pro Gln Val Thr Pro Lys Lys Ser Cys Ser
            20                  25                  30

Leu Ser Lys Tyr Gln Phe Pro Ala Pro Leu Glu Leu Lys Ala Val Trp
        35                  40                  45

Arg Met Lys Glu Gln Phe Glu Asp Ile Met Leu Leu Thr Asn Arg Lys
    50                  55                  60

Cys Asn Thr Arg Leu Phe His Arg Lys Trp Asp Ile Ala Glu Leu Ser
65                  70                  75                  80

Val Pro Asp Arg Ile Thr Leu Val Glu Ala Glu Leu Asp Leu Thr Ile
                85                  90                  95

Thr Val Leu Thr Asn Pro Thr Thr Gln Arg Leu Ala Glu Thr Cys Gln
            100                 105                 110

Gln Pro Leu Ala Phe Leu Thr Gln Val Gln Glu Asp Leu Arg Asp Cys
        115                 120                 125

Leu Ala Leu Glu Ala Pro Ser His Gln Pro Ser Gly Lys Leu Arg His
    130                 135                 140

Trp Leu Gln Lys Leu Lys Thr Ala Lys Lys Glu Thr Ala Gly Cys
145                 150                 155                 160

Leu Glu Ala Ser Ala Ile Leu His Ile Phe Gln Val Leu Asn Asp Leu
                165                 170                 175

Arg Cys Ala Ala Gln Arg Glu Asp Cys Thr
            180                 185

<210> SEQ ID NO 20
<211> LENGTH: 196
<212> TYPE: PRT
<213> ORGANISM: D. rerio

<400> SEQUENCE: 20

Met Thr Ser Lys Gln Lys Val Phe Gly Ser Arg Gly Thr Arg Gly Arg
1               5                   10                  15

Val Trp Lys Arg Gln Pro Glu Ile Arg Trp Asn Gln Ser Gln Ser Ser
            20                  25                  30

Ala Ser Thr Cys Glu Trp Leu Gly Arg Tyr Arg Ile Ile Thr Thr Glu
        35                  40                  45

Ser Leu Asn Leu Leu Lys Asn Met Gly Gly Lys Tyr Ala Asp Leu Glu
    50                  55                  60

Thr Pro Phe Pro Ser Arg Leu Tyr Phe Leu Met Asp Lys Ser Lys Val
65                  70                  75                  80

Glu Asp Gln Val Lys Phe Leu Val Leu Thr Leu Asp His Ile Ile His
                85                  90                  95

Leu Met Asp Ala Arg Glu His Met Asn Ser Val Asn Trp Asp Gln Asn
            100                 105                 110

Thr Val Glu Asp Phe Leu Asn Ile Leu His Arg Lys Ser Ser Asp Leu
```

```
               115                 120                 125
Lys Glu Cys Val Ala Arg Tyr Ala Lys Pro Ala His Lys Glu Ser Tyr
        130                 135                 140

Glu Ile Arg Ile Lys Arg His Phe Arg Thr Leu Lys Lys Ile Leu Lys
145                 150                 155                 160

Lys Lys Gln Tyr Ser Ala Glu Ala Trp Glu Gln Ile Arg Arg Val Val
                165                 170                 175

Lys Ser His Leu Gln Arg Met Asp Ile Ile Ala Ser Asn Ala Arg Val
            180                 185                 190

Asn Pro Arg Val
        195
```